United States Patent
Zalevsky et al.

(10) Patent No.: US 10,724,846 B2
(45) Date of Patent: Jul. 28, 2020

(54) SYSTEM AND METHOD FOR USE IN DEPTH CHARACTERIZATION OF OBJECTS

(71) Applicant: CONTINUSE BIOMETRICS LTD., Tel Aviv (IL)

(72) Inventors: Zeev Zalevsky, Rosh HaAyin (IL); Javier Garcia, Valencia (ES); Nisim Nisan Ozana, Rehovot (IL); Ran Califa, Givataym (IL); Moshe Arie Ariel Schwarz, Bnei Brak (IL)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 0 days.

(21) Appl. No.: 16/303,295

(22) PCT Filed: May 23, 2017

(86) PCT No.: PCT/IL2017/050574
§ 371 (c)(1),
(2) Date: Nov. 20, 2018

(87) PCT Pub. No.: WO2017/203525
PCT Pub. Date: Nov. 30, 2017

(65) Prior Publication Data
US 2019/0212124 A1     Jul. 11, 2019

Related U.S. Application Data

(60) Provisional application No. 62/349,750, filed on Jun. 14, 2016, provisional application No. 62/340,264, filed on May 23, 2016.

(51) Int. Cl.
| | | |
|---|---|---|
| *G01N 21/21* | (2006.01) | |
| *G01B 9/02* | (2006.01) | |
| *G01B 11/16* | (2006.01) | |
| *G01N 21/47* | (2006.01) | |

(Continued)

(52) U.S. Cl.
CPC ........ *G01B 9/02095* (2013.01); *G01B 11/162* (2013.01); *G01N 21/4795* (2013.01);
(Continued)

(58) Field of Classification Search
CPC ........ G01N 1/30; G01N 1/31; G01N 33/4833; G01N 33/5058; G01N 1/34; G01N 1/40;
(Continued)

(56) References Cited

U.S. PATENT DOCUMENTS 8,638,991 B2    1/2014  Zalevsky et al.
9,733,460 B2 *  8/2017  Kang ................. G02B 21/0064
(Continued)

FOREIGN PATENT DOCUMENTS

WO    2014/020611 A1    2/2014

OTHER PUBLICATIONS

Supplementary partial European Search Report of EP17802327 dated Jan. 21, 2020.
(Continued)

*Primary Examiner* — Michael P Stafira
(74) *Attorney, Agent, or Firm* — Browdy and Neimark, PLLC

(57) ABSTRACT

A system is described, for use in optical measurement of a sample. The system comprising: an illumination unit configured for providing coherent illumination of one or more selected wavelength ranges and directing it onto one or more selected inspection regions of the sample, a collection unit configured for collecting light returning from the inspection region and generating output data comprising a sequence of image data pieces indicative of secondary speckle patterns formed at an intermediate plane in optical path of light collection, a depth resolving module configured for affecting at least one of the illumination unit and the collection unit for determining an association between collected secondary (Continued)

speckle patterns and depth layers of the sample; and a control unit being connectable to said depth resolving module and configured for operating said depth resolving module and for receiving said sequence of image data pieces from the collection unit and processing said sequence of image data pieces by determining correlation functions between at least portions of said secondary speckle patterns associated with corresponding depth layers of the sample, thereby determining one or more parameter variations along depth of the sample.

17 Claims, 14 Drawing Sheets

(51) Int. Cl.
*G06T 7/514* (2017.01)
*A61B 5/00* (2006.01)
*G01N 21/17* (2006.01)
*G01H 9/00* (2006.01)

(52) U.S. Cl.
CPC ............ *G06T 7/514* (2017.01); *A61B 5/0051* (2013.01); *A61B 5/0084* (2013.01); *G01H 9/00* (2013.01); *G01N 21/1717* (2013.01); *G01N 21/21* (2013.01); *G01N 2021/479* (2013.01); *G01N 2021/4711* (2013.01); *G01N 2201/06113* (2013.01); *G06T 2207/10101* (2013.01); *G06T 2207/20056* (2013.01); *G06T 2207/30024* (2013.01)

(58) Field of Classification Search
CPC ..... G01N 2001/305; G01N 2001/4038; G01N 27/44743; G01N 27/44747; G01N 33/5088; G01N 33/53; G01N 11/00; G01N 2011/0073; G01N 2021/4711; G01N 2021/479; G01N 21/1717; G01N 21/21; G01N 21/4795; G01N 2201/06113; G01N 2203/0044; G01N 2203/0089; G01N 2800/52; G01N 33/02; G01N 33/383; G01N 33/48; G01N 33/502; G01N 33/5026; G01N 33/92; G01N 3/12; A61B 5/0066; A61B 3/102; A61B 3/12; A61B 3/14; A61B 3/0008; A61B 3/10; A61B 5/0077; A61B 5/6803; A61B 3/028; A61B 3/085; A61B 3/113; A61B 5/0059; A61B 3/022; A61B 3/024; A61B 3/063; A61B 3/066; A61B 3/08; A61B 3/1035; A61B 3/1216; A61B 3/13; A61B 3/165; A61B 5/01; A61B 5/0476; A61B 5/0496; A61B 5/14532; A61B 5/1455; A61B 5/14555; A61B 3/1015; A61B 2562/0204; A61B 2562/0219; A61B 2562/0247; A61B 5/0084; A61B 3/0025; A61B 3/101; A61B 5/0035; A61B 5/0073; A61B 3/1241; A61B 5/0088; A61B 5/7257; A61B 5/0075; A61B 3/1005; A61B 5/0042; A61B 5/6852; A61B 8/10; A61B 2576/026; A61B 3/005; A61B 3/107; A61B 3/1225; A61B 5/00; A61B 5/046; A61B 5/4064; A61B 5/6814; A61B 8/461; A61B 90/37; A61B 1/00172; A61B 1/043; A61B 1/06; A61B 2090/3735; A61B 2562/0233; A61B 34/20; A61B 3/152; A61B 5/0071; A61B 5/0082; A61B 5/02007; A61B 5/14553; A61B 5/4547; A61B 5/7425; A61B 8/12; A61B 1/00057; A61B 1/07; A61B 2034/105; A61B 2034/2065; A61B 2090/365; A61B 2090/376; A61B 2562/04; A61B 2576/02; A61B 3/00; A61B 3/0041; A61B 3/1025; A61B 3/1233; A61B 3/18; A61B 5/0051; A61B 5/0062; A61B 5/0068; A61B 5/0086; A61B 5/1076; A61B 5/4848; A61B 5/4851; A61B 5/6844; A61B 5/725; A61B 6/5247; A61B 8/0841; A61B 8/4416; A61B 8/5261; A61B 17/3421; A61B 1/00016; A61B 1/0002; A61B 1/00032; A61B 1/00156; A61B 1/00165; A61B 1/041; A61B 1/227; A61B 1/24; A61B 2034/107; A61B 2034/2055; A61B 2034/2057; A61B 2090/364; A61B 2090/371; A61B 2090/378; A61B 2090/3937; A61B 2090/3979; A61B 2090/3983; A61B 2505/05; A61B 2560/0223; A61B 2562/0238; A61B 2562/0266; A61B 2562/046; A61B 2562/228; A61B 2576/00; A61B 34/00; A61B 34/10; A61B 34/25; A61B 3/0016; A61B 3/0033; A61B 3/0058; A61B 3/0091; A61B 3/103; A61B 3/117; A61B 3/1208; A61B 3/135; A61B 5/0064; A61B 5/0093; A61B 5/0097; A61B 5/021; A61B 5/0215; A61B 5/026; A61B 5/0261; A61B 5/04001; A61B 5/0402; A61B 5/065; A61B 5/14552; A61B 5/415; A61B 5/418; A61B 5/42; A61B 5/441; A61B 5/442; A61B 5/4528; A61B 5/4542; A61B 5/4552; A61B 5/4875; A61B 5/6817; A61B 5/6826; A61B 5/6853; A61B 5/6862; A61B 5/7203; A61B 5/7217; A61B 5/7228; A61B 5/7264; A61B 5/7267; A61B 5/7435; A61B 5/748; A61B 6/12; A61B 6/14; A61B 6/469; A61B 6/504; A61B 8/0891; A61B 8/4488; A61B 8/4494; A61B 8/485; A61B 8/488; A61B 8/5223; A61B 8/5269; A61B 90/39; G02B 21/34; G02B 21/367; G01B 11/162; G01B 9/02095
See application file for complete search history.

(56) References Cited

U.S. PATENT DOCUMENTS

| | | | |
|---|---|---|---|
| 2009/0040527 A1* | 2/2009 | Popescu | G01B 9/02035 356/491 |
| 2010/0121200 A1 | 5/2010 | Carvalho et al. | |
| 2011/0125004 A1 | 5/2011 | Thumma et al. | |
| 2012/0105858 A1 | 5/2012 | Popescu et al. | |
| 2013/0144137 A1 | 6/2013 | Zalevsky et al. | |
| 2014/0036272 A1* | 2/2014 | Nadkarni | G01N 21/4795 356/450 |
| 2014/0148658 A1 | 5/2014 | Zalevsky et al. | |
| 2014/0343411 A1* | 11/2014 | O'Brien | A61B 5/7257 600/425 |
| 2017/0120337 A1* | 5/2017 | Kanko | B22F 3/1055 |
| 2017/0248518 A1* | 8/2017 | Nadkarni | G01N 21/4788 |

OTHER PUBLICATIONS

Mariampillai A et al: "Speckle variance detection of microvasculature using swept-source optical coherence tomography", Optics Letters, Optical Society of America, US, vol. 33, No. 13, Jul. 1, 2008, pp. 1530-1532.

(56) References Cited

OTHER PUBLICATIONS

Vicente Mico et al: "Three-dimensional shape measurement by means of depth-to-coherence coding of the object shape", Proceedings of SPIE, vol. 7389, Jun. 15, 2009, p. 73893E.
Valera J D et al: "Combined fibre optic laser velocimeter and electronic speckle pattern interferometer with a common reference beam", Measurement Science and Technology, IOP, Bristol, GB, vol. 4, No. 5, May 1, 1993, pp. 578-582.

* cited by examiner

APPLYING CONTINUOUS STIMULATION ONTO A SAMPLE 1010

COHERENTLY ILLUMINATING A REGION OF THE SAMPLE AND COLLECTING LIGHT RETURNING FROM THE SAMPLE 1020

INTERFERRING COLLECTED LIGHT WITH REFERENCE BEAM HAVING VARYING OPTICAL PATH 1030

GENERATING AND COLLECTING CORRESPONDING SPECKLE PATTERNS 1040

PROCESSING A COLLECTED SEQUENCE OF SPECKLE PATTERNS TO GENERATE DEPTH RESOLVED DATA ABOUT SAMPLE RESPONSE 1050

FIG. 4

RECEIVING A SEQUENCE OF IMAGE DATA PIECES 2010

DETERMINING ONE OR MORE SETS OF SPECKLE PATTERN REGIONS HAVING SIMILAR FLICKERING FREQUENCY 2020

GENERATING CORRESPONDING ONE OR MORE SETS OF IMAGE DATA PIECES OF CORRESPONDING SPECKLES REGION 2030

ANALYZING EACH SET OF CORRESPONDING SPECKLE PATTERN AND DETERMINING CORRELATION BETWEEN SPECKLE REGIONS OF THE SET 2040

COMPAINGT DATA ABOUT CORRELATION OF SPECKLE PATTERNS WITH DATA ABOUT STIMULATION APPLIED TO THE SAMPLE 2050

GENERATING LAYERED DATA ABOUT RESPONSE TO STIMULATION BY THE SAMPLE 2060

FIG. 5

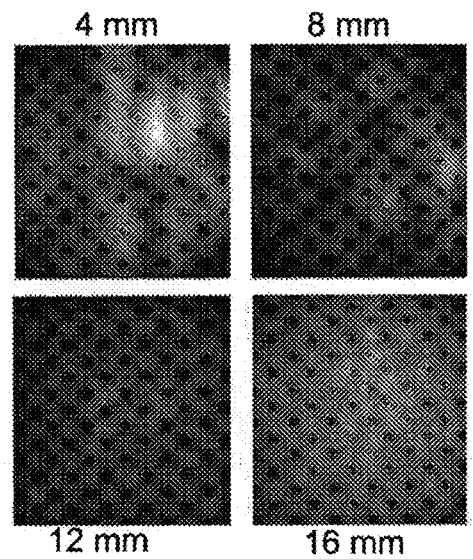
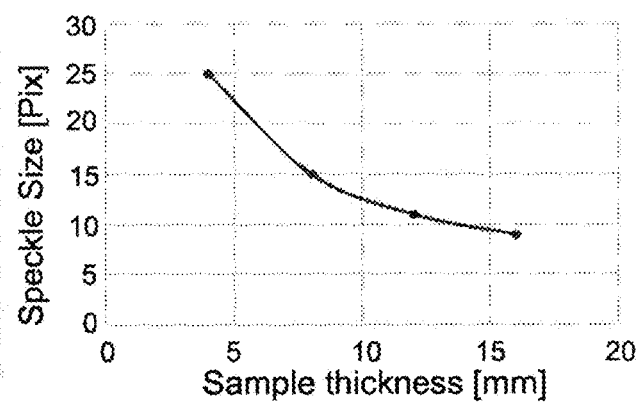
FIG. 6A  FIG. 6B
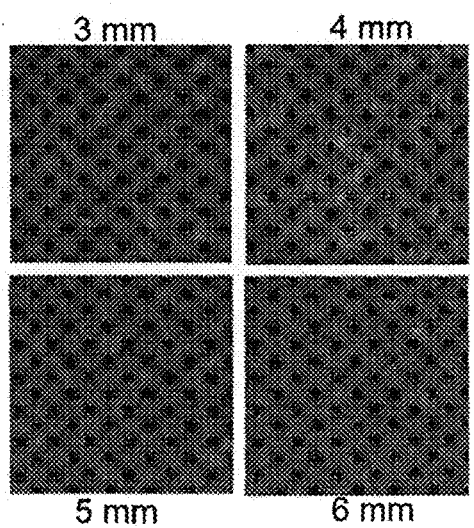
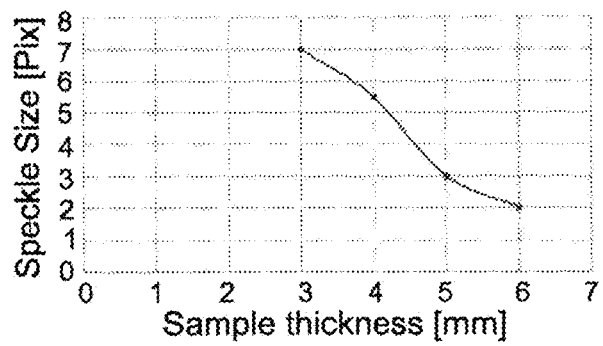
FIG. 6C  FIG. 6D

SYSTEM AND METHOD FOR USE IN DEPTH CHARACTERIZATION OF OBJECTS

TECHNOLOGICAL FIELD

The present invention is in the field of optical measurements of sample parameters and movement and is in particular relevant for three-dimensional characterization of tissue parameters and layers. In some configurations, the present invention relates to measurement of elasticity parameters within a volume of the tissue.

BACKGROUND

The term Elastography relates to measurement of elastic properties of materials. Elastographic measurements are typically used to in analysis of biological tissue to determine various sample parameters such as bone density and accumulation of deposition within the tissue.

Generally, elastographic measurements include generating a distortion in the sample and collecting data about response of the sample to the distortion within certain time window. Detection of the sample response is conventionally performed using various techniques between ultrasound imaging, magnetic resonance imaging and optical coherent tomography.

Several techniques have been developed for monitoring data on vibrations of a sample's surface. Such techniques utilize optical inspection of the sample and analyzing of secondary speckle patterns formed by reflection and scattering of coherent light from an inspection region on the sample's surface.

U.S. Pat. No. 8,638,991 presents a method for imaging an object. The method comprises imaging a coherent speckle pattern propagating from an object, using an imaging system being focused on a plane displaced from the object.

US 2013/0144137 and US 2014/0148658 present a system and method for use in monitoring one or more conditions of a subject's body. The system includes a control unit which includes an input port for receiving image data, a memory utility, and a processor utility. The image data is indicative of data measured by a pixel detector array and is in the form of a sequence of speckle patterns generated by a portion of the subject's body in response to illumination thereof by coherent light according to a certain sampling time pattern. The memory utility stores one or more predetermined models, the model comprising data indicative of a relation between one or more measurable parameters and one or more conditions of the subject's body. The processor utility is configured and operable for processing the image data to determine one or more corresponding body conditions; and generating output data indicative of the corresponding body conditions.

GENERAL DESCRIPTION

There is a need in the art for a novel technique for providing elastographic measurements of samples. The present invention enables surface as well as depth resolved monitoring of parameters of a sample. Generally, the present technique is directed at monitoring material parameters, e.g. elastography measurements of a sample utilizing optical inspection that can be performed remotely and non-invasively. The technique typically utilizes speckle-based monitoring of sample parameters. To this end, the present technique uses coherent illuminations and detection of speckle patterns generated by scattering of the coherent illumination from the sample, while incorporating the use of a depth resolving module operable for affecting at least one of illumination and collection of light returning from the sample to enable association between at least portions of the collected speckle patterns and corresponding depth layers of the sample.

Accordingly, the system of the present invention comprises an illumination unit configured for providing and directing coherent illumination of one or more wavelength ranges onto one or more selected inspection regions on the sample; a collection unit configured for collecting light returning from said one or more inspection regions and generate accordingly at least one sequence of image data pieces, each corresponding to secondary speckle patterns formed at an intermediate plane located between the inspection region and the collection unit; a depth resolving unit configured for affecting at least one of the illumination unit and the collection unit for determining an association between data in the collected secondary speckle patterns and depth layers of the sample at the inspection region; and a control unit being connectable to the depth resolving module and being configured and operable for operating said depth resolving module and for receiving sequence of image data pieces from the collection unit and processing and analyzing said sequence of image data pieces by determining correlation functions between at least portions of said secondary speckle patterns associated with corresponding depth layers of the sample. The control unit may utilize the so determined correlation functions for determining one or more parameter and their corresponding variations along certain depth of the sample at the one or more inspection region.

To this end the depth resolving unit may utilize one or more optical effects associated with reflection and/or scattering of light components from different depths of the sample. In this connection, it should be noted that although typically any wavelength range has certain depth of penetration into various samples. The actual penetration depth of light illuminated on the sample depends on various parameters including; sample material, wavelength of light, and angle of incident of the illumination onto the surface of the sample. Such penetration depth may typically vary between a few nanometers and up to a few centimeters. Accordingly, the present technique utilizes at least one of variation in properties of light components providing data on different depth layers of the sample. Such optical properties include: variation in optical path between light components returning from different layers, variation in general dimensions of speckles formed by self-interference of light components returning from different layers, variation of angular intensity map of light components returning from different layers, and axial path of light components undergoing scattering within depth of the sample.

In some embodiments, the present technique may enhance differentiation between depth layers utilizing suitable contrast material injected into the sample. Such suitable contrast material may e.g. include selected nanoparticles having varying reflection propertied with respect to light components of one or more wavelength and/or polarization. Accordingly, the reflection and scattering of light from different layers of the sample is affected by the concentration of the contrast material enhancing differentiation between depth layers.

Generally, variations in the speckle patterns detected over time provide indications to variations in shape, curvature, orientation and location of the inspected region. In some embodiments, the present technique also utilizes a stimulation unit configured for applying selected stimulation (e.g.

ultrasound stimulation) to the sample, enabling detection and monitoring of elastic response of the sample material along certain depth of penetration (of the illumination). In some configurations, the stimulation applied to the sample may take part in determining association between speckle pattern data, or portion thereof, and layers of the sample to which the speckle data corresponds.

According to some embodiments, the depth resolving unit may utilize an interferometric unit comprising a reference arm and configured for directing a reference beam provided by the illumination unit along said reference arm for combining the reference beam with light collected from the inspection region. The interferometric depth resolving unit is configured for modulating optical path of said reference arm to enable modulation of the interference patterns formed by combining light propagated in said reference arm with light returning from the inspection region. Accordingly, the image data piece collected by the collection unit are indicative of interfering speckle patterns generated by interference between light returning from the sample through the sample arm and a reference beam travelling thorough said reference arm. To provide depth resolved elastographic data, the technique of the present invention utilizes modulation of optical path of a reference beam. Interference between the sample beam reflected/scattered from the inspected region and the reference beam generates a speckle pattern indicative of scattering/reflection of the beam from certain corresponding depth within the sample.

To this end the present invention provides a system for use on elastographic measurements, the system comprising a coherent light source (e.g. laser light source) configured to emit light in one or more predetermined wavelength range; an optical arrangement configured for splitting the emitted light to form a sample beam and a reference beam; direct the sample beam to a region of a sample and collect and re-merge paths of the sample and reference beams; and a detector unit configured for collecting data about interference between the sample and reference beam to thereby generate image data of secondary speckle pattern. The optical arrangement is further configured to modulate optical path of the reference beam in a predetermined temporal pattern to thereby vary interference pattern formed by interference of the collected sample and reference beams.

As a result of the modulation of the optical path of the reference beam, the collected speckle pattern generated by scattering from the sample surface is superimposed with interference fringes varying in time in accordance with variations of the reference beam path. The technique of the present invention utilizes variation in the interference fringes pattern to differentiate between speckle patterns associated with light reflection/scattering of different depths within the surface of the sample, to thereby provide volumetric (three-dimensional) data about the sample.

Further, generally to provide elastographic data about the sample, the system may further comprise a stimulation generating unit configured to stimulate the sample (e.g. by ultrasound waves) to thereby generate certain vibration response from the sample. The detector unit collects a sequence of image data pieces, each corresponding to a speckle pattern from the sample. This allows processing of the collected sequence of data pieces to determine properties of different depths of light penetration into the sample providing three-dimensional resolution to elastographic measurements.

According to some other embodiments, the present technique may utilize depth resolving through spatial/axial distribution of light scattering from the sample. To this end, the depth resolving module may be configured as a varying aperture configured for selectively affecting spot size of illumination or field of view of collection of light returning from the inspection region. More specifically, in some examples, the technique may utilize illuminating the inspection region with a spot of certain size, and collecting light returning through a field of view being a portion of the spot size, when the spot size in increase (without change to field of view of collection), the collected light provides data indicative on additional layers of the sample. Similarly, using a certain selected spot size for illumination, and collecting light returning from the sample with plurality of fields of view, varying by size of region from which the light is collected, provides data on various depths of the sample.

In some other exemplary embodiments, the present technique utilizes effects of variation in angular scattering between different layers, or depths, within the sample. In such configurations, light components are provided to impinge on the inspection region with a plurality of different angular directions, and the returning light components are collected and processed in accordance with data on angular variation for determining the about the sample and/or sample response to external stimulation.

To this end the system may generally comprise a light source assembly comprising a plurality (e.g. two, three or more) of light sources, each configured to emit coherent illumination with a selected predetermined wavelength range; and a collection unit comprising an optical detector, and an optical arrangement configured for collecting light returning from the sample and transmit it to the detector unit. Additionally, the system comprises a depth resolving module, which in these embodiments may be configured as a polychromatic filter, and/or one or more additional detector arrays enabling of separation of input data based on wavelength in accordance with the plurality of selected wavelength ranges of the light sources.

This technique may also utilize a light collection unit comprising a sensor array and an optical arrangement. The optical arrangement is configured to collect light returning from the inspection region of the sample with relatively low numerical aperture (NA) and direct the collected light onto the sensor array. Thus, configured for light collection from a relatively small field of view, limiting angular variation of collected light. The optical arrangement is further configured to provide defocused image of the collected light on the sensor array, or more specifically, to image an intermediate plane on the sensor array. This results with an image, on the detector array, being indicative of a secondary speckle pattern generated from the scattered light. As the light source assembly provides coherent illumination in a plurality of wavelength ranges, the collected image data corresponds to a superposition of plurality of speckle patterns respectively.

Thus, according to a broad aspect of the present invention, there is provided a system for use in optical measurement of a sample; the system comprising: an interferometric speckle pattern collection units comprising a sample arm directing coherent illumination onto a region of a sample and a reference arm, optical path of the reference arm being modulated to provide varying interference between the sample arm and the reference arm, and a detector array configured to collect a sequence of image data pieces associated of interfering speckle patterns generated by interference between light returning from the sample through the sample arm and a reference beam travelling thorough the reference arm; and a control unit configured and operable to receive image data pieces from the detector array and to analyze and process said image data pieces to determine depth resolved data about the sample.

According to some embodiments, the system may further comprise a stimulating unit configured for applying a predetermined stimulation onto the sample to thereby enable detection of sample response to said predetermined stimulation.

Typically, optical path modulation of the reference arm may be provided by varying location of a mirror of the reference are within a predetermined axial range, said mirror being moved at constant acceleration along one direction of the axial range and is returned to its original location.

According to some embodiments, alignment of illumination and collection along the sample arm may be configured to provide depth independent interference pattern within one or more speckles. This is such that the number of fringes per speckle is configured to be depth dependent.

The optical path of the reference arm may be temporally modulated, e.g. by varying the movement of the mirror in a time modulated fashion that provides an orthogonal coding to the speckle pattern flickering, thereby providing orthogonal variation of speckle flickering associated with different penetrations depths. This is substantially similar to the spread spectrum approach, such that the change in the flickering frequency is not monotonically related to the axial distance but rather corresponds to an orthogonal code.

According to some embodiments, the illumination source may be configured to apply at least one of temporal and spatial coherence variation to light illuminating the sample to thereby provide orthogonal axial encoding to collected light components in accordance with axial penetration depth into the sample. This provides shaping of the illumination source such that the coherence function encodes the axial information in an orthogonal manner (as in spread spectrum approach) to better perform the axial separation of data in addition to the flickering pattern of the speckles.

According to another broad aspect of the invention, the present invention provides a system for use in optical measurement of a sample, the system comprising:

an illumination unit configured for providing coherent illumination of one or more selected wavelength ranges and directing the coherent illumination onto one or more selected inspection regions of the sample, a collection unit configured for collecting light returning from the inspection region and generating output data comprising a sequence of image data pieces indicative of secondary speckle patterns formed at an intermediate plane located between the inspection region and the collection unit, a depth resolving module configured and operable for affecting at least one of the illumination unit and the collection unit for determining an association between data in the collected secondary speckle patterns and depth layers of the sample at the inspection region; and a control unit being connectable to said depth resolving module and configured and operable operating said depth resolving module and for receiving said sequence of image data pieces from the collection unit and processing and analyzing said sequence of image data pieces by determining correlation functions between at least portions of said secondary speckle patterns associated with corresponding depth layers of the sample, and for determining one or more parameter variations along depth of the sample at said one or more inspection region.

The system may further comprise a stimulating unit configured for applying a predetermined stimulation onto the sample to thereby enable detection of sample response to said predetermined stimulation.

According to some embodiments, the depth resolving module may be configured as an interferometric unit comprising a reference arm utilizing a reference illumination beam provided by the illumination unit, and configured for modulating optical path of said reference arm and combining light propagated in said reference arm with light returning from the inspection region thereby causing the collection unit for collecting image data piece associated of interfering speckle patterns generated by interference between light returning from the sample through the sample arm and a reference beam travelling thorough said reference arm. The optical path modulation of the reference arm may be provided by varying location of a mirror of the reference arm within a predetermined axial range. In some embodiments, the location of the mirror may be moved at constant acceleration along one direction of the axial range and is returned to its original location. In some other embodiments, the modulation may be associated with sinusoidal or square profile of the mirror's movement at a selected frequency.

The optical path of the reference arm may be modulated at a selected frequency selected to complete at least one modulation cycle within integration time of the collection unit. When stimulation of the sample is used, the sample may be stimulated at frequency $v_1$, the reference beam may be modulated at frequency $v_2$ such that integration time is longer than $1/v_1$ and $1/v_2$, however the integration time may preferably be selected to be shorter than $1/(|v_1-v_2|)$.

In some embodiments, alignment of illumination and collection along the sample arm may be configured to provide depth independent interference pattern within one or more speckles.

The optical path of the reference arm may be temporally modulated in an orthogonal code thereby providing orthogonal variation of speckle flickering associated with different penetrations depths.

In some embodiments, said illumination unit is configured to apply at least one of temporal and spatial coherence variation to light illuminating the sample to thereby provide orthogonal axial encoding to collected light components in accordance with axial penetration depth into the sample.

Generally, in some embodiments, the control unit may comprise a flickering detection module configured and operable for receiving said sequence of image data pieces and identifying at least one portion of frame having repetitive flickering and for marking speckle pattern associated with said at least one portion of the frame as relating to depth layer in accordance with frequency of said repetitive flickering, thereby enabling separate processing of speckle pattern portions associated with separate depth layers of the sample.

According to yet some embodiments, the said illumination unit may comprise a plurality of light sources emitting coherent illumination of corresponding plurality of different wavelength ranges and having plurality of optical axes respectively; said collection unit is configured for generating a sequence of polychromatic image data pieced corresponding to a secondary speckle patterns of said light returning from the sample collected at a predetermined sampling rate; and said depth resolving module comprises a pre-processing utility and configured for separating data corresponding with speckle patterns of different wavelength ranges from image data pieces of said sequence, thereby enabling the control unit for determining corresponding correlation functions between speckle patterns of each wavelength range for determining one or more parameter variations along depth of the sample at said one or more inspection region. The plurality of wavelength ranges may be selected as having different penetration depths into the sample in accordance with optical parameters of the sample.

According to yet some other embodiments, the depth resolving module may be configured as aperture variation module configured for affecting aperture of at least one of the illumination unit and collection unit.

The illumination unit may be configured for illumination said inspection region forming an illumination spot of a selected dimension, said depth resolving module comprises a varying aperture unit configured for selectively varying field of view of said collection unit. The field of view of collection, varying selectively, may be smaller with respect to dimension of said illumination spot.

Alternatively, the depth resolving module may comprise a varying aperture unit configured for selectively varying illumination spot generated by said illumination unit on said inspection region, said collection unit is configured for collecting light returning from said inspection region with a field of view of a selected dimension. The field of view of collection may be larger with respect to dimension of the illumination spot.

According to yet some other embodiments, the illumination unit may be configured for providing coherent illumination of predetermined polarization level, said depth resolving module comprises a polarization measurement unit configured and operable for determining data indicative of degree of polarization of collected light; the control unit is further configured and operable for receiving said data indicative of degree of polarization and determine depth level associated to image data piece in accordance with level of loos of polarization of the collected light. The polarization measurement unit may be configured for providing data indicative of Stokes parameters of collected light.

Generally the above described technique may utilize enhancement of association between data in the collected secondary speckle patterns and depth layers of the sample at the inspection region variation of concentration of one or more selected contrast materials injected into the sample.

According to yet another broad aspect, the present invention provides a system for use in optical measurement of a sample; the system comprising:
an interferometric speckle pattern collection units comprising a sample arm directing coherent illumination onto a region of a sample and a reference arm, optical path of the reference arm being modulated to provide varying interference between the sample arm and the reference arm, and a detector array configured to collect a sequence of image data pieces associated of interfering speckle patterns generated by interference between light returning from the sample through the sample arm and a reference beam travelling thorough the reference arm;
and a control unit configured and operable to receive image data pieces from the detector array and to analyze and process said image data pieces to determine depth resolved data about the sample.

In some embodiments, the system may further comprise a stimulating unit configured for applying a predetermined stimulation onto the sample to thereby enable detection of sample response to said predetermined stimulation.

The optical path modulation of the reference arm may be provided by varying location of a mirror of the reference are within a predetermined axial range, said mirror being moved at constant acceleration along one direction of the axial range and is returned to its original location.

In some embodiments, the alignment of illumination and collection along the sample arm is configured to provide depth independent interference pattern within one or more speckles.

The optical path of the reference arm may be temporally modulated in an orthogonal code thereby providing orthogonal variation of speckle flickering associated with different penetrations depths.

In some embodiments, the illumination source may be configured to apply at least one of temporal and spatial coherence variation to light illuminating the sample to thereby provide orthogonal axial encoding to collected light components in accordance with axial penetration depth into the sample.

According to yet another broad aspect, the present invention provides a system comprising: illumination unit configured for illuminating an inspection region with coherent illumination of a selected wavelength range and selected spot size; collection unit configured for collecting light returning from said illumination spot through selected collection aperture and generating sequence of image data pieces associated with speckle patterns formed at an intermediate plane between said inspection region and said collection unit; and a control unit; the control unit is configured and operable for receiving from the collection unit one or more sequences of image data pieces associated with selected values of at least one of illumination spot size and aperture of light collection and for determining, for each sequence of image data piece collection with a selected value of at least illumination spot size and aperture of light collection, a correlation function being correlation between speckle patterns in consecutive image data piece, and for using one or more correlation functions for determining variation of one or more parameters along depth of said sample.

According to yet another broad aspect, the present invention provides a system for use in optical measurement of a sample, the system comprising:
an illumination unit comprising a plurality of light sources emitting coherent illumination with corresponding plurality of different wavelength ranges and a having a plurality of optical axis respectively;
a collection unit configured to collect light returning from the sample and to generate a plurality of polychromatic image data pieced corresponding to a secondary speckle patterns of said light returning from the sample collected at a predetermined sampling rate; and
a control unit configured for receiving said plurality of image data pieces, and for separating data corresponding with speckle patterns of different wavelength ranges to thereby determine, for each wavelength range, correlation data between speckle patterns in sequential image data pieces to thereby determine depth resolved data about the sample.

The plurality of wavelength ranges may be selected as having different penetration depths into the sample.

The collection unit may be configured for collecting light returning from a selected point on the sample with a low numerical aperture, thereby limiting the field of view thereof to illumination spot size on the inspection region or a portion thereof.

According to yet another broad aspect, the present invention provides a method for monitoring a sample, the method comprising:
providing coherent illumination onto a selected inspection region on the sample;

collecting light components scattering from said inspection region and causing light interference with a reference beam having optical path varying with a selected modulation frequency;

generating a sequence of image data piece corresponding to intermediate plane of said light interference;

processing said sequence of image data piece and determining one or more sets of speckle pattern region having repetitive flicker with defined frequency;

analyzing said one or more sets of speckle pattern region and determining corresponding one or more correlation functions between speckle pattern regions in said sequence of image data piece, each correlation function being indicative of variation in light scattering from a corresponding depth layer of the sample; and generating layered data about variation of one or more sample parameters along depth layers thereof.

The method may further comprise applying external stimulation of a selected stimulation frequency on the sample. The selected modulation frequency and said selected stimulation frequency may be selected to be greater with respect to integration time of image data piece generation. This while a difference between the frequencies may be smaller with respect to integration time, thereby enabling detection of different flickering frequencies of speckle in varying sizes.

In some embodiments, the method may further comprise injecting one or more selected contrast material to the sample, thereby enhancing variation of light reflection or scattering properties in accordance with contrast materials properties.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 4 exemplifies a method for determining depth resolve parameters of a tissue or an element according to some embodiments of the invention;

FIG. 5 exemplifies a method for processing input data for determining depth resolve parameters of a sample according to some embodiments of the invention.

FIGS. 6A to 6D show experimental results illustrating variation in average speckle size in accordance with sample thickness, FIGS. 6A and 6C show image data of measured speckle patterns and FIGS. 6B and 6D show average size data for transmission and reflection measurements respectively;

DETAILED DESCRIPTION OF EMBODIMENTS

Figure 1:
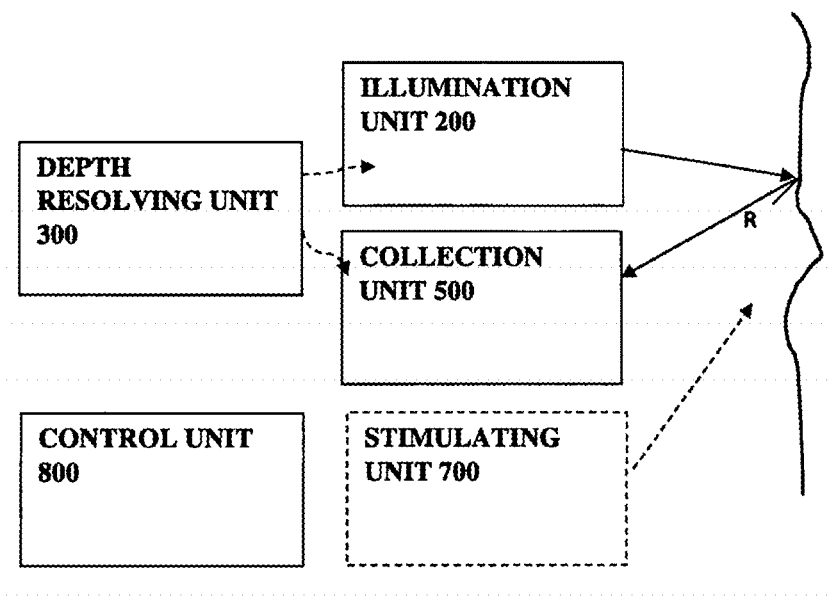
FIG. 1 illustrates, in a way of a block diagram, a system for depth characterization of a sample according to some embodiments of the invention.

Reference is made to FIG. 1 schematically illustrating a system 100 for use in determining parameters of a sample. The system 100 includes an illumination unit 200, collection unit 500, depth resolving unit 300 and a control unit 800. The system may also include a stimulation unit 700. The illumination unit 200 may typically include a light source unit, and is configured and operable for providing coherent illumination of one or more wavelength ranges and direct the illumination onto one or more inspection regions R of a sample. The collection unit generally includes an imaging lens arrangement and a detector array and is configured for collecting light returning from the one or more inspection regions R and generate corresponding one or more sequences of image data pieces corresponding to secondary speckle patterns formed by light self-interferences at an intermediate plane between the inspection region R and the collection unit 500. More specifically, the imaging lens arrangement is located in optical path of light propagating from the inspection region R toward the detector array, at a location that provides imaging of an intermediate plane in path of the collected light. Thus, self-interference of light components form the collected secondary speckle patterns.

The control unit 800 generally includes a processing utility and is configured and operable for receiving input data corresponding with the one or more sequences of image data pieces from the collection unit, and for processing the input data for determining selected parameters of the sample. To this end the control unit is configured for determining correlation function indicative of spatial correlations between speckle patterns in temporally consecutive image data piece. The correlation function is indicative of variations in location and orientation of the inspection region.

To enable the system 100 to differentiate between image data piece, or portions thereof, associated with light reflection or scattering from different depth layers of the sample, the system 100 utilizes a depth resolving module 300. The depth resolving module 300 is configured for affecting at least one of illumination and collection of light from the inspection region R to thereby enable association between at least portions of the image data pieces and different layers, depths of light penetration, of the sample. Generally, the depth resolving module 300 utilizes one or more optical parameters associated with depth of penetration of light into the sample such as changes in optical path, variation in speckle size, average spot area and angular distribution of light reflection.

In some configurations of the system 100, the depth resolving module 300 utilizes a reference arm and corresponding reference beam provided from the illumination unit 200. The reference beam is combined with light returning from the sample such enabling collection of image data pieces associated with speckle patterns of interference between the collection illumination and the reference beam. In this connection, reference is made to FIG. 2 illustrating system 100 according to some embodiments utilizing interferometric depth resolving module 500.

Figure 2:
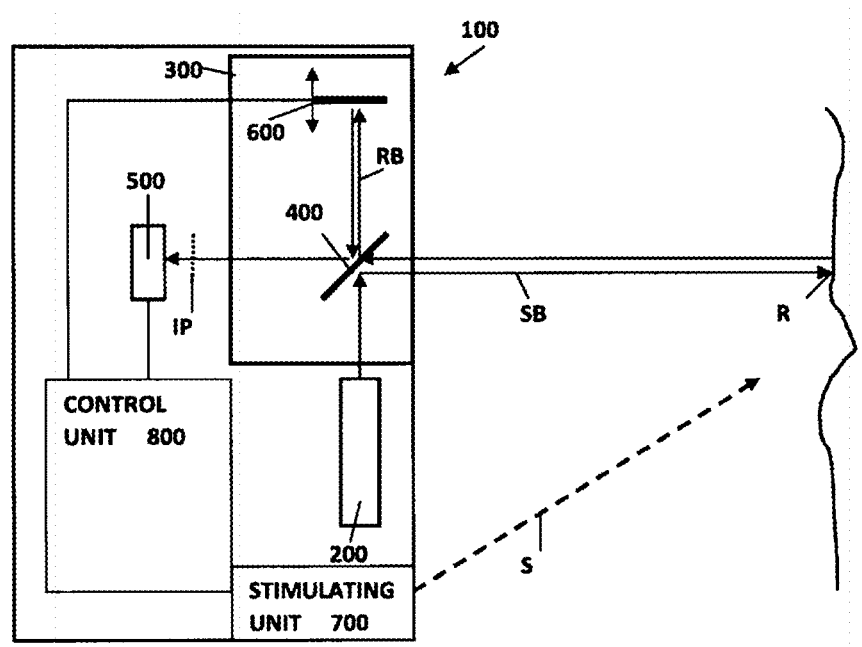
FIG. 2 schematically illustrates a system for use in depth characterization and for determining parameters of a tissue according to some embodiments of the present invention.

In the example of FIG. 2, the system 100 includes an illumination unit (light source) 200 configured to generate coherent illumination in one or more predetermined wavelength ranges, a depth resolving module configured as an optical arrangement 300 directing light onto a sample and collecting light returning from the sample, and a collection unit (detector unit) 500 configured for collecting light returning from the sample and generating a sequence of image data pieces corresponding to light returning from the sample. The system may also include a stimulating unit 700 configured for generating certain stimulation onto the sample and a control unit 800 configured for receiving sequence of image data pieces from the detector and data about the generated stimulation and to process the received data to determined one or more parameters about the sample.

The optical arrangement 300 of the depth resolving unit generally includes a light splitting unit 400 (beam splitter) splitting light emitted from the light source unit 200 to direct a portion of the light SB towards a region R of the sample being inspected, and a portion of the light RB to a reference beam path. The sample beam SB, returning from the sample, is merged again with the reference beam RB, e.g. by the beam splitter 400, to form interference between the sample beam and the reference beam.

The collection unit 500 is configured to collect image data associated with an intermediate plane IP along path of the collected light. This allows detection of a secondary spackle pattern generated from self-interference of the sample beam while scattering from the sample. It should be noted that although the system illustrated in FIG. 2 is exemplified with normal incidence of light, the system may be configured to illuminated the sample and collect light returning (reflected and scattered) from the sample at angles, which may be equal or not. However, in some embodiments, the collection unit 500 may utilize a polarizer filter configured for blocking light components associated with specular reflection to thereby collect light components associated with scattering of light from the inspection region.

To provide depth resolve data about the sample, the optical arrangement is configured to modulate optical path of the reference beam to thereby generate interference fringes superimposed on the spackle pattern of the collected light. To this end the optical arrangement includes a moveable mirror 600 configured for varying optical path of the reference arm RB. The mirror 600 is moveable, e.g. using a motor or a piezoelectric crystal, within a predetermine range. Typically, the mirror 600 may be moveable with various selected modulation patterns. According to some embodiments, the modulation pattern may include a series of pulses of contact acceleration forming sow-tooth movement pattern. In some other embodiments, the modulation pattern may be of square profile (contact speed to one direction, and constant speed returning to original location) or sinusoidal. The optical path modulation of the reference beam causes variation in the interference fringes between consecutive image data pieces as collected by the detector unit 500. Operating at a selected predetermined sampling rate, the interference fringes generate flickering of the speckle pattern. Light components returning (reflected and/or scattered) from different penetration depths into the sample form constructing interference with the references beam at corresponding optical paths of the reference beam. As the mirror 600 temporally modulated the optical path of the reference beam; speckle pattern components associated with light returning from different depth in the sample are thus modulated accordingly.

As indicated above, in some embodiments the optical path of the reference beam RB may be modulated by moving the mirror 600 at constant acceleration within each cycle. More specifically, the mirror starts at position 0 (zero) and is moved at a predetermined acceleration until it reached the end of its movement range (e.g. 1 cm). At this stage the mirror is moved back to position 0 and is moved again. Thus, the velocity of the mirror at each location x can be described as:

$$V(x) = \sqrt{V_0^2 + 2ax} \quad \text{(equation 1)}$$

where $V(x)$ is the mirror velocity at position x, $V_0$ is the mirror initial velocity (typically $V_0=0$), and a is the acceleration. It should be noted that typically the mirror's 600 movement range is selected to be comparable (or equal) to penetration depth of the optical illumination into the sample.

As a result of the varying length of the reference path, speckle patterns associated with different penetration depth into the sample flicker at rates, corresponding to a ratio between the mirror's velocity for corresponding reference length, having phase variation of 0, $2\pi$ etc. from the sample beam. Thus, the flickering rate associated with each reference beam length is (assuming $V_0=0$):

$$v(x) = \frac{V(x)}{\lambda} = \frac{\sqrt{2ax}}{\lambda} \quad \text{(equation 2)}$$

where $\lambda$ is the wavelength of illumination. This modulation causes speckle patterns associated with different penetration depths in the sample to appear (flicker) at frequency that corresponds with the penetration depth, or with a penetration depth having optical length that corresponds to suitable location (x) of the mirror 600. This is under a justified assumption that the location x of the mirror 600 can be associated with depth information based on correspondence of optical paths for the signal (illumination) beam and the reference beam.

According to some other embodiments of the invention, the depth resolving module 300, configured as interferometric unit as exemplified in FIG. 2, may be configured for modulating optical path of the reference beam at a selected frequency $V_m$, while the system 100 utilizes a stimulation unit 700 configured for applying stimulation of frequency $v_s$ on the sample.

The control unit 800 may be configured to receive a sequence of image data pieces from the detector unit 500, while operating the stimulating unit 700 to generate predetermined stimulation S on the sample. Within the sequence of received image data pieces, the control unit is configured to determine speckle patterns, or portion of patterns, occurring or flickering at certain different frequencies, to thereby identify variations is speckle patterns corresponding to different depth within the sample. For each flickering frequency, the control unit may operate to determine parameters of the corresponding depth of the sample by processing variation in the speckle pattern in response to stimulation S applied on the sample, e.g. as described in patent publication US 2014/0148658 incorporated herein by reference in relation to determining parameters of a sample under stimulation using variation of detected speckle pattern. It should be noted that although the system illustrated in FIG. 2 is configured with normal incidence of light, the system may be configured to illuminated the sample and collect light returning (reflected and scattered) from the sample at angles, which may be equal as in specular reflection or not.

Figure 3:
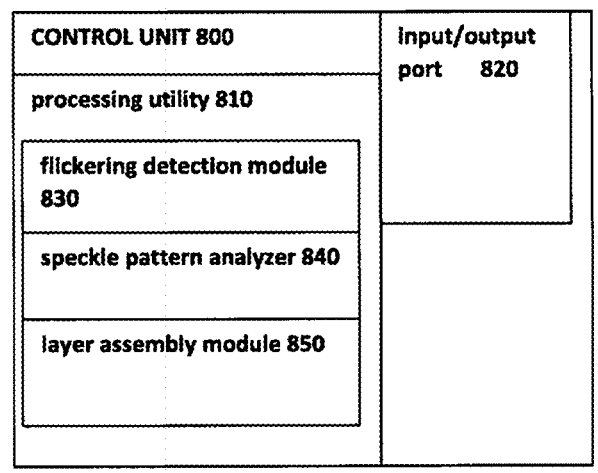
FIG. 3 illustrates schematically a configuration of the control unit according to some embodiments of the invention.

Reference is made to FIG. 3 illustrating control unit 800. The control unit 800 typically includes a processor utility 810 and input/output port 820 for receiving image data from the detector unit 500 and for operating the moveable mirror 600, stimulating unit 700 and light source 200, as well as network communication and/or user interface. The processor utility 810 includes a flickering detecting module 830 configured for determining sets of image data pieces associated with speckles flickering at certain flickering frequency and to distinguish between sets of different flickering frequencies (corresponding to different penetration depths); and a speckle pattern analyzer 840 configured and operable for receiving a set of image data pieces associated with a common speckle flickering frequency and to analyze data about variation of the speckle pattern within the set of image data pieces in combination with data about stimulation applied to the sample to determine data about stimulation response of the sample.

The processing utility 810 may generally also include a layer assembly module 850. The layer assembly module is configured and operable to receive data about stimulation response as determined from different sets of image data pieces, corresponding to different flickering frequencies. The layer assembly module is further configured for processing said data about stimulation response in accordance with data about the flickering frequencies and corresponding locations of the moveable mirror 600 to determine a layered structure of the sample. Such layered structure of the sample includes depth resolved stimulation response data of the sample indicating elastic parameters of the sample within certain penetration depth of the wavelength range of the optical illumination.

The speckle pattern analyzer 840 is typically configured and operable to determine local correlation functions between speckle patterns appearing in consecutive image data pieces within a set of image data pieces corresponding to a common flickering frequency of the speckles. It should be noted that different portions of an image data piece may be associated with different flickering frequencies as the sample may or may not be flat.

In this connection, the present technique may typically be used for determining elastographic data about biological tissue while not damaging the tissue, e.g. using visible or infra-red illumination. Additionally, or alternatively the present technique may be used for any other type of sample such as plastic, metal, minerals etc. Such determined elastographic data may be used for determining state of the material as well as to identify material properties.

Although described herein as utilizing constant acceleration movement of the mirror 600, the technique of the present invention may be used with various other patterns of reference beam optical length variations. It should be noted that constant acceleration provides a change in flickering frequency that is monotonic with the depth, however alternative movement patterns of the mirror 600 may also provide unique correspondence between flickering frequency of speckle patterns (due to interference fringes) and depth penetration of the light in the sample. Such other modulation patterns are typically selected to generate a spread spectrum (temporal spectrum) orthogonal encoding unique per each layer of light penetration.

Reference is made to FIG. 4 exemplifying operation method according to the present technique. A sample, typically being placed at a sample holding position or such that the system may be directed at, is provided and certain continuous stimulation is applied thereto 1010. At the same time, the light source 200 is operated and the system shines coherent illumination onto a region of the sample to be inspected 1020. Light returning from the sample is collected to form input data. The collected light is interfered with a reference beam 1030, such that the optical path of the reference beam is modulated. The collected interfered light is detected at an intermediate plane to generate data about speckle patterns associated with the sample response to stimulation 1040. The collected sequence of image data pieces corresponding to speckle patterned is processed to determine depth resolved data about sample response to the stimulation 1050. The determined data is depth resolved due to variation in interference patterns as the optical path of the reference beam is modulated.

Processing of the collected sequence of image data pieces is exemplified in FIG. 5. As shown, the control unit is operable for receiving a sequence of image data pieces associated with plurality of detected speckle patterns 2010. The processing further includes determining one or more sets of regions in the sequence of image data pieces, having speckle pattern portions flickering with common frequency 2020. Such common frequency generally corresponds to speckles generated at common penetration depth on the illuminating onto the sample. For simplifying the processing, the technique may also include generating corresponding one or more sets of the image data pieces of the common frequency speckle regions 2030. These generated sets undergo processing of variations in the speckle patterns 2040 by determining correlation between speckle patterns in consecutive image data pieces of the set. The technique includes analyzing data about the correlation function, typically in combination with data about the stimulation applied to the sample, to determined data about response function of the sample 2050. The data of different sets may be combined to form a three-dimensional map of response function within different penetration depths into the sample 2060 providing depth resolved response data of the sample.

It should be noted that penetration depth on illuminating into the sample may typically depend on illumination wavelength range as well as on optical properties of the sample. For various biological materials, such penetration depth may be of the range of 1-2 centimeter and may thus include relatively large portion of the sample material. Providing response function, and data about material parameter corresponding not only to the surface of the sample but also to different depths within the sample may be highly useful in analyzing of various materials being biological or not.

The depth resolution of the data determined by the present technique may be associated with temporal resolution at which the flickering of the speckles can be separated (each flickering frequency is associated with different axial distance). This is different than the conventionally known depth resolved technique of optical coherent tomography (OCT)

where the axial resolution is related to either the coherence of the illumination source (non-coherent wide spectrum source have better resolution) or the spectral range at which the scanning of the illumination source is performed. According to the present technique, the temporal dependence of the axial resolution is much simpler to control and management and relates directly to modulation pattern of the optical path of the reference beam.

According to some embodiments, speckle pattern portions associated with light components returning from different layers may be identified and differentiated based on variation in dimension between the average speckle sizes. The present technique is based on the inventors understanding that speckle patterns associated with light components returning/scattering from different layers of the sample vary in average dimension of the speckle. Additionally, the different layers may response to external stimulation with similar frequency and certain, not always constant, phase shift.

Generally, the illumination impinging on the inspection region can be described as creating electric field $E_1$ at first depth, which generates speckle patterns having an averaged speckle size of $d_1$. Additionally, electric field $E_2$ is formed at another depth of the sample, and results in generating speckle patterns with an average size of $d_2$. Generally, the use of imaging lens arrangement with selected suitable focal length thereof provides optics of the imaging lens arrangement in which light coming from different depths creates speckle patterns with different speckle dimensions. For simplicity, the first and second speckle patterns may be modeled using sinusoidal form, e.g., as:

$$s_1(x) \approx \cos^2\left(\frac{\pi x}{d_1} + \varphi_1\right) = \frac{1}{2} + \frac{1}{2}\cos\left(\frac{2\pi x}{d_1} + \varphi_1\right) \quad \text{(equation 3)}$$

$$s_2(x) \approx \cos^2\left(\frac{\pi x}{d_2} + \varphi_2\right) = \frac{1}{2} + \frac{1}{2}\cos\left(\frac{2\pi x}{d_2} + \varphi_2\right)$$

It should be noted that the sinusoidal representation of the speckle pattern is incomplete, and can estimate only a portion of the speckle pattern including a few adjacent speckles. However, such model accurately and simply illustrates interference as described further below.

Under external stimulation, provided by the stimulation unit 700, the different layers/depths of the sample response with substantially similar frequency $v_1$, but with varying amplitudes and relative phase shift. The corresponding speckle patterns are affected by vibrations of the layers at corresponding frequency $v_1$ and amplitudes of $d > d_1$, $d_2$ providing:

$$s_1(x - V_1 t) \approx \cos^2\left(\frac{\pi}{d_1}(x - V_1 t) + \varphi_1\right) = \quad \text{(equation 4)}$$

$$\frac{1}{2} + \frac{1}{2}\cos\left(\frac{2\pi}{d_1}(x - V_1 t) + \varphi_1\right)$$

$$s_2(x - V_1 t) \approx \cos^2\left(\frac{\pi}{d_2}(x - V_1 t + \delta x(t)) + \varphi_2\right) =$$

$$\frac{1}{2} + \frac{1}{2}\cos\left(\frac{2\pi}{d_2}(x - V_1 t + \delta x(t)) + \varphi_2\right)$$

here: $V_1 = dv_1$ and $\delta x(t)$ is a temporal shift between elastic response of the different layers and may be between 0 and d. The temporal shift generally destroys the synchronization between the different (two in this example) inspected layers of the sample.

As described above, the depth resolving module 300 is configured for generating interference between light collected from the sample and a reference beam propagating a modulated optical path varying at frequency $v_2$. The collection unit 500 is configured for collecting the so generated pattern at a selected intermediate plane. Accordingly, the collected electric field can be represented as:

$$E_{out}(x,t) = s_1(x - V_1 t) + s_2(x - V_1 t) + r(x - V_2 t) \quad \text{(equation 5)}$$

where the reference field is typically a tilted planar wave with angular frequency of a and can be represented as:

$$r(x - V_2 t) = \exp(2\pi i \alpha(x - V_2 t)) \quad \text{(equation 6)}$$

here $V_2$ is the movement velocity of the reference beam (mirror 600) and is equal to $v_2/\alpha$.

The electric field of equation 5 is collected by a detector array of the collection unit 500 and accordingly is collected by intensity integrated over exposure/integration time. Thus, the collected image data can be represented as:

$$I_{out}(x) = \int |E_{out}(x,t)|^2 dt = 1 + \int |s_1(x - V_1 t)|^2 dt + \int |s_2(x - V_1 t)|^2 dt + \text{Re } al\{\int s_1(x - V_1 t) s_2^*(x - V_1 t) dt + \int r^*(x - V_2 t)(s_1(x - V_1 t) + s_2(x - V_1 t)) dt\} \quad \text{(equation 7)}$$

Generally, the integration time of the detector array may be much larger than the modulation cycle of the stimulating field ($1/v_1$) or and modulation of the reference beam ($1/v_2$), but may be selected to be smaller than $1/(v_1 - v_2)$. Thus, the collected intensity pattern, forming a corresponding image data piece is:

$$I_{out}(x) = 1 + c_1 + c_2 + \text{Real}\{\int r^*(x - V_2 t)(s(x - V_1 t) + s_2(x - V_1 t)) dt\} \quad \text{(equation 8)}$$

where $c_1$ and $c_2$ are space independent constants and the cross-correlation expression between $s_1$ and $s_2$ vanishes as the field distributions of the speckle patterns $s_1$ and $s_2$ are not correlated to each other (having different dimensions and have non synchronized movement due to $\delta x(t)$). More specifically, within integration time of the detector array (of the collection unit 500) the cross-correlation expression is considered to vanish within the integration time, thus $\int s(x - V_1 t) s_2^*(x - V_1 t) dt = 0$. Accordingly, the collected image data is left with data associated with correlations between $s_1$ or $s_2$ and the reference beam, in the forms of Re $al\{r^*(x - V_2 t) s_1(x - V_1 t) dt\}$ and Re $al\{\int r^*(x - V_2 t) s_2(x - V_1 t) dt\}$.

Using equation 4 above, and general assumption on spatial coordinates provides:

$$\text{Real}\{r^*(x - V_2 t) s_1(x - V_1 t)\} \approx \quad \text{(equation 9)}$$

$$\frac{1}{2}\cos(2\pi\alpha V_2 t) + \frac{1}{2}\cos\left(-\frac{2\pi}{d_1} V_1 t + \varphi_1\right)\cos(2\pi\alpha V_2 t)$$

$$\text{Real}\{r^*(x - V_2 t) s_2(x - V_1 t)\} \approx$$

$$\frac{1}{2}\cos(2\pi\alpha V_2 t) + \frac{1}{2}\cos\left(-\frac{2\pi}{d_2} V_1 t + \varphi_2\right)\cos(2\pi\alpha V_2 t)$$

Resulting after time integration with:

$$\text{Real}\left\{\int r^*(x - V_2 t) s_1(x - V_1 t) dt\right\} = \frac{1}{2}\int \cos(2\pi\alpha V_2 t) dt + \quad \text{(equation 10)}$$

$$\frac{1}{2}\int \sin\left(-\frac{2\pi}{d_1} V_1 t + \varphi_1\right)\sin(2\pi\alpha V_2 t) dt +$$

$$\frac{1}{2}\int \cos\left(2\pi t\left(\alpha V_2 - \frac{V_1}{d_1}\right) + \varphi_1\right) dt$$

-continued $$\text{Real}\left\{\int r^*(x-V_2 t)s_2(x-V_1 t)dt\right\} = \frac{1}{2}\int \cos(2\pi\alpha V_2 t)dt +$$
$$\frac{1}{2}\int \sin\left(-\frac{2\pi}{d_2}V_1 t + \varphi_2\right)\sin(2\pi\alpha V_2 t)dt +$$
$$\frac{1}{2}\int \cos\left(2\pi t\left(\alpha V_2 - \frac{V_1}{d_2}\right) + \varphi_2\right)dt.$$

Generally, the spatial periodicity a and inverse dimension of the speckle patterns $1/d_1$ may preferably be of the same order of magnitude, i.e. angle of reference beam providing spatial frequency thereof is selected to be of the order of $1/d_1$. Additionally, the integration time of the collection unit 500 is preferably selected to be relatively long, generally longer that $d/V_1$ and $1/\alpha V_2$ and preferably much longer. As a result, the first two terms of both expressions vanish (since they change at temporal frequency of $\alpha V_2$ or of $V_1/d_1$). Accordingly, the remaining terms in both expression change (flicker) at temporal frequencies of:

$$v_{F1} = \alpha V_2 - V_1/d_1$$

$$v_{F2} = \alpha V_2 - V_1/d_2 \quad \text{(equation 11)}$$

Accordingly, the system 100 may preferably be configured, in accordance with stimulation frequency $v_1$, reference beam modulation frequency $v_2$ and angular/spatial frequency $\alpha$, in view of variation of speckle average dimensions $d_1$ and $d_2$, to provide the flickering frequencies $v_{F1}$ and $v_{F2}$ to be efficiently sampled by the collection unit 500. More specifically, the sampling rate of the collection unit is preferably selected to comply with Nyquist frequencies associated with the greater of $v_{F1}$ and $v_{F2}$. In other words, the sampling rate (proportional to the integration time) is preferably faster than $1/v_{F1}$ and $1/v_{F2}$. Thus, the third term in both expressions provides flickering between image data pieces and does not average to zero.

Accordingly, the present technique utilizes external stimulation (e.g. ultrasound) of selected frequency $v_1$ combined with modulation of a reference beam at selected frequency $v_2$ thereby enabling to remove cross terms associated with interference of light components arriving from different layers of the sample. While maintaining terms associated with interference of light components of each layer and the known reference beam. Thus, enabling differentiation between portions of speckle patterns associated with different layers of the sample, using different flickering frequencies for each layer. It should be noted that the present technique is described herein using two layers for simplicity. Additional layers may be used, providing substantially similar results of varying flickering frequencies for the different layers.

As indicated above, the control unit 800 may generally be configured for detecting portions of the collected image data pieces, associated with corresponding flickering frequencies, to thereby determine association between portions of the speckle patterns and corresponding depth layers of the sample.

Reference is made to FIGS. 6A to 6D showing experimental results indicating variation in average dimension of speckles associated with varying depth layers of a sample. FIG. 6A shows speckle patterns formed by light transmitted through samples of thickness 4 mm, 8 mm, 12 mm and 16 mm; FIG. 6B shows a graph indicating average speckle size formed by light transmission through samples of several widths; FIG. 6C shows speckle patterns formed by light reflected from samples of thickness 3 mm, 4 mm, 5 mm and 6 mm; and FIG. 6D shows corresponding graph of speckle dimension vs. sample thickness.

The setup providing transmission results is based on a lensed fiber coupled laser diode (830 nm) light source with a spot diameter of 20 um. Tissue samples of various thickness (3 mm-6 mm) were synthesized from a mixture of agaros (1% concentration) and intralipid (0.1% concentration). The transmitted laser scattering speckle pattern was captured for each sample separately by a CMOS camera (pixelink) with a lens (f=75 mm) and polarizer that was tuned to block the component of the ballistic part (light transmitted without scattering) of the incoming light.

The reflection setup is based on a green laser diode (532 nm) propagating through a 100 um pinhole to give a small spot diameter. Again, tissue samples of various thickness (3 mm-6 mm) were synthesized from a mixture of agaros (1% concentration) and intralipid (0.1% concentration). The reflected laser scattering speckle pattern was captured for each sample separately by a CMOS camera (pixelink) with a lens (f=75 mm) and polarizer that was tuned to block the component of the specular reflection leaving only the part of the scattered reflection light.

Figure 7A:
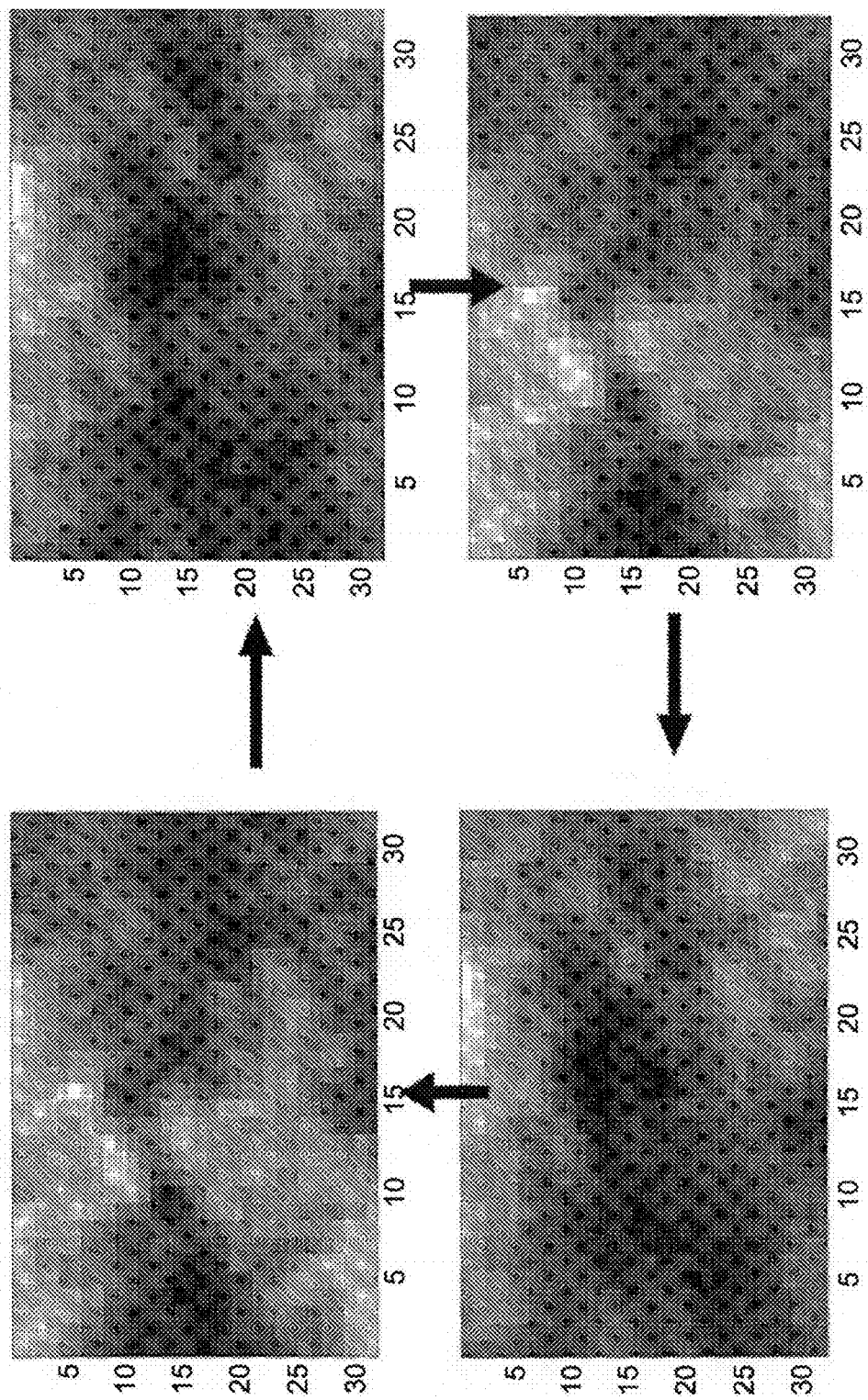
FIGS. 7A to 7D show experimental results of flickering speckles in consecutive images (FIG. 7A) flickering frequency spectra obtained for speckles of different dimensions (FIGS. 7B and 7C) and cut-off frequencies obtained for speckles having different dimensions (FIG. 7D)
Figure 7B:
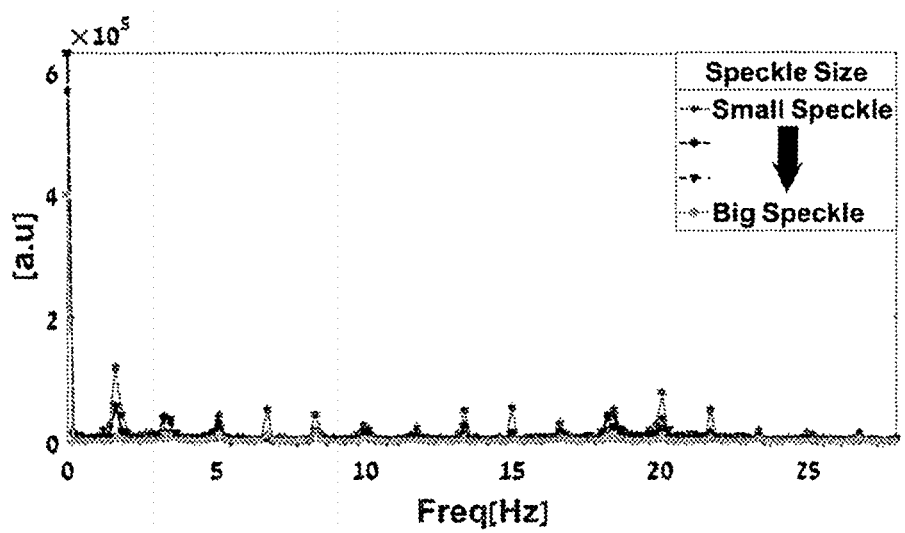
Figure 7C:
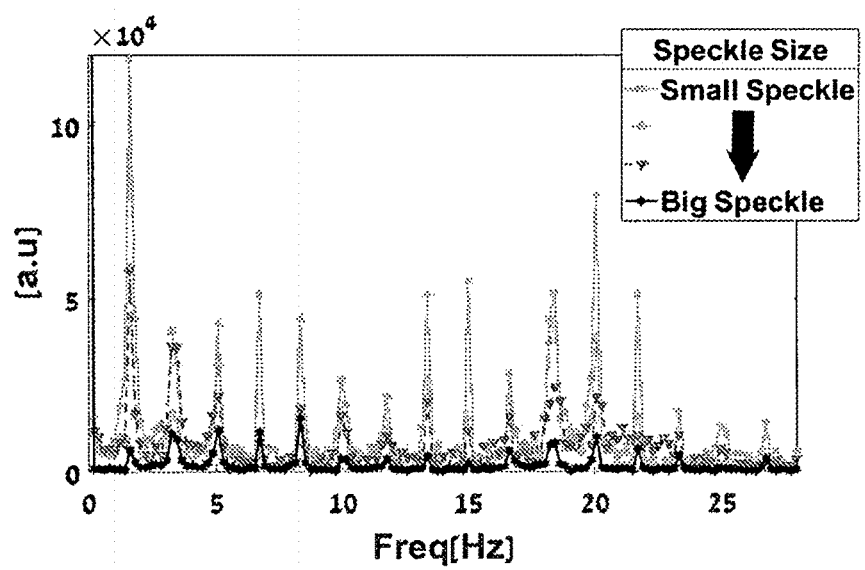
Figure 7D:
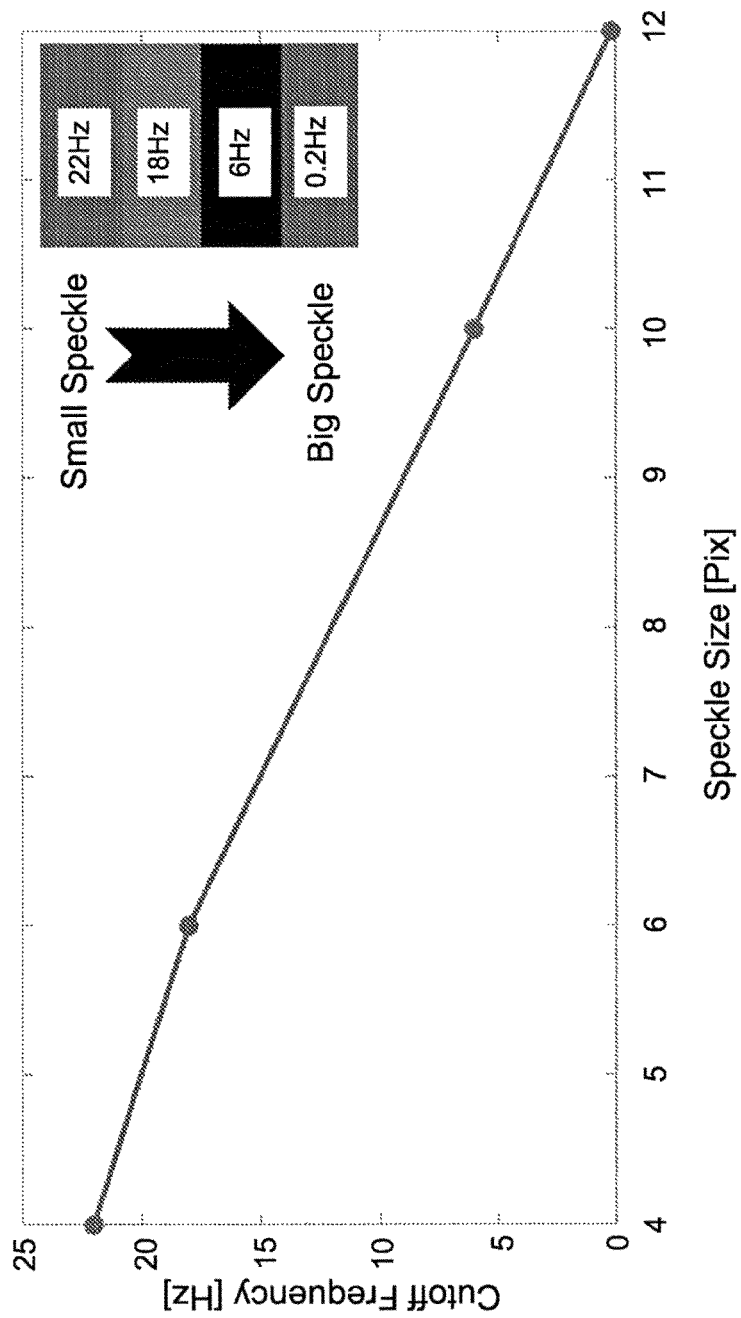

Reference is further made to FIGS. 7A to 7D, illustrating experimental results showing flickering speckles in consecutive images (FIG. 7A) flickering frequency spectra obtained for speckles of different dimensions (FIG. 7B and FIG. 7C) and cut-off frequencies obtained for speckles having different dimensions (corresponding to photons coming from different depths of the inspected tissue) in FIG. 7D. As can be seen from These figures, a significant variation exists in flickering frequencies, and corresponding cut off frequency of the flickering, for light returning from different depths of the sample. This enables the control unit 800, and flickering detection module 830 thereof, to differentiate between portions of collected speckle patterns associated with light/photons coming from different depths of the sample, and separate the corresponding portions for independent processing.

It should be noted that the present technique provides optical separation between light components associated with different layers of the sample. This separation in the photonic level due to temporal modulation and demodulation makes the present technique robust with respect to digital and electronic signal to noise restrictions that are very dominant in post-processing depth resolving techniques.

According to some other embodiments, the depth resolution technique provides separation of the layers based on the temporal resolution of the sampling camera and its capability to separately capture image data pieces associated with different temporal encodings of speckle flickering. As described above, the mirror 600 of the reference beam RB may be moved at constant acceleration for each cycle thereof, the flickering frequency is root like, in a way similar to a time lens. Assuming repetition of N flickering of the same speckle region is require to identify the frequency, the temporal resolution for distinguishing between depth layer data is:

$$\delta t = \frac{N}{v(x)} \quad \text{(equation 12)}$$

where $\delta t$ is the temporal difference between flickering of distinguished sets of speckle regions. Given the frequency $v(x)$ in equation 2 above provides:

$$t(x) = \sqrt{\frac{2x}{a}} \quad \text{(equation 13)}$$

providing depth resolution of:

$$\delta x = \delta t \sqrt{2ax} \quad \text{(equation 14)}$$

Similarly, the depth resolution may be given as a parameter of number of samples used for processing, using again equation 2 above provides:

$$\delta x = \lambda N \quad \text{(equation 15)}$$

From another point of view the temporal spectrum resolution $\delta v$ is limited by the time used for measuring each flickering point:

$$\delta v = \frac{1}{\delta t} = \frac{v(x)}{N} \quad \text{(equation 16)}$$

which may be derived to provide:

$$\delta v = \delta x \left( \frac{\sqrt{a}}{\lambda \sqrt{2x}} \right) \quad \text{(equation 17)}$$

and again, simplified using equation 16 resulting in:

$$\delta x = \frac{2\Delta x}{N} \quad \text{(equation 18)}$$

This provides that the depth resolution according to the present technique relates to wavelength of illumination light, and movement of the modulated mirror 600 of the reference beam. Additionally, such depth resolution may be improved by increasing number of image data pieces used for determining sets of flickering speckles. More specifically, the depth resolution of the present technique may be given by $$\delta x = \sqrt{2\lambda \Delta x} \quad \text{(equation 19)}$$

It should be noted that this resolution limit relates to separation between different axial layers of the object/tissue being inspected utilizing variation of flickering frequencies. However, additional parameters of the measurement system relate to axial separation and may eventually provide increased SNR to thereby yield better performance.

One additional parameter associated with separation between axial layers of the sample relate to coherent length of the illumination source. More specifically, if the illuminating source provides optical illumination having relatively short coherence length, different axial layers will not contribute to interference between light components. This results in separation between speckle patterns associated with different axial penetration depths.

Additionally, axial resolution may also be determined in accordance with geometry and alignment of the measurement system 100. The numerical aperture (NA) of the illumination path provided by the light source unit and that of light collection path is preferably designed to increase interference fringes between light components returning from close layers within single speckles. The numerical aperture may be designed using selected of aperture diameter and optical power of the lenses used as well as by utilizing one or more spherically aberrated lenses in front of the detector. Increased number of interference fringes within a single speckle of the detected speckle pattern results with increased flickering of the speckles as a result of movement of the mirror 600. If for example the are two interference fringes inside a single speckle, proper axial scanning of the mirror causes shift in location of the fringes to move and thus flickering of the speckle. If there are two fringes within a speckle, the flickering frequency is doubles as a result of mirror movement. Thus, even if the mirror 600 is moved, for scanning, with constant velocity, speckles characterized as having two fringes within the speckle will flicker with double frequency and enable separation of data associated with the corresponding layers.

It should be noted that the above described parameters, accelerating movement of the mirror 600, illumination coherence length and optical and NV design, are generally stand alone and may be used to provide depth resolved inspection of a sample. However, the technique of the invention may utilize a combination of any pair of these measurement techniques or a combination of the three of them to improved depth resolution in sample inspection. Further, the system 100 of the present invention may preferably configured to utilize all three of the above described techniques to thereby increase signal to noise ratio (SNR) at which the axial information is obtained to thereby provide better overall performance.

In this connection, it should also be noted that the total axial resolution of the system may exceed the limit described on equation 19. More specifically, in some configurations the coherence length for illumination may be selected to be sufficiently short such that at certain position of the mirror, interference is shown only between collected light components arriving from substantially the same depth. This reduces interference fringes resulting from light components returning from different depths/layers and especially from the entire inspected volume.

Thus, as mentioned above, the use of speckle flickering with different flickering frequencies for separating between axial layers may benefit from the use of relatively short coherence length. However, as these parameters are independent, the final SNR at which the axial information is extracted may typically be higher than that would be obtained if only the approach of short coherence length is used (e.g. as done in time domain OCT techniques).

Thus, differently than the conventional Optical coherence tomography (OCT) techniques, the technique of the present invention utilizes temporal and spatial coherence shaping of collected light to provide encoding of the collected light in accordance with axial penetration depth in the sample. This is in contrary to the use of sinusoidal variation of the illumination coherence length as used in Fourier domain OCT to provide extraction of the axial information by applying inverse Fourier transform. According to the present technique, the temporal and also the spatial coherence of the illumination source provide substantially orthogonal basis of coding (as in spread spectrum approach) to allow a different decoding between the multiplexed depth information. Thus, the use of speckle flickering frequencies in combination with short coherence length may further enhance the axial information extraction.

Figure 8:
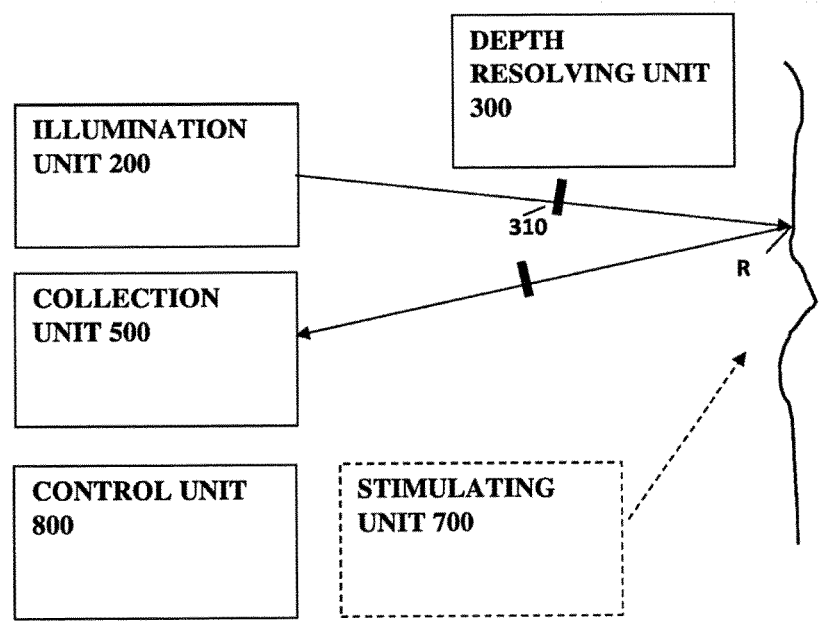
FIG. 8 illustrates schematically a system utilizing varying aperture unit for depth resolving monitoring of a sample.

According to yet some other embodiments, the present technique may utilize effects of light components (photons) scattering within the sample matter and corresponding statistical analysis of Brownian excursions modifying trajectories of the scattering light components for resolving data about different depths of the sample. In this connection, reference is made to FIG. 8 exemplifying system 100 configured according to some embodiments of the invention. In these exemplary embodiments, the depth resolving module generally includes an aperture variation unit 310 configured for affecting light components impinging on the inspection region R, or field of view of the collection unit 500. The aperture variation unit 310 may be located in optical path of light propagating from the illumination unit 200 onto the inspection region R, and configured for selectively adjusting illumination spot size on the inspection region R. alternatively, the aperture varying unit 310 may be location in optical path of light returning from the inspection region R and collected by the collection unit 500, or being an element of the imaging lens arrangement, and configured for selectively varying field of view of the collection unit.

Figure 9A:
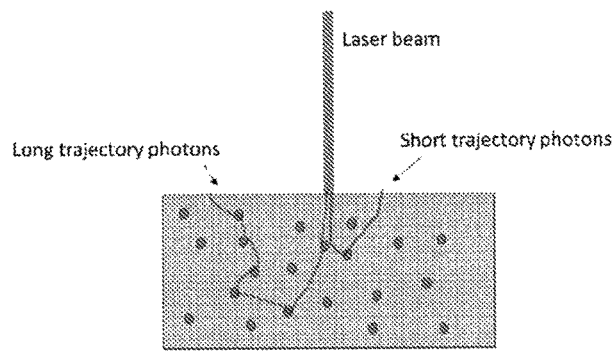
FIGS. 9A and 9B exemplify effects of scattering from different layers and random walk distribution in axial location.
Figure 9B:
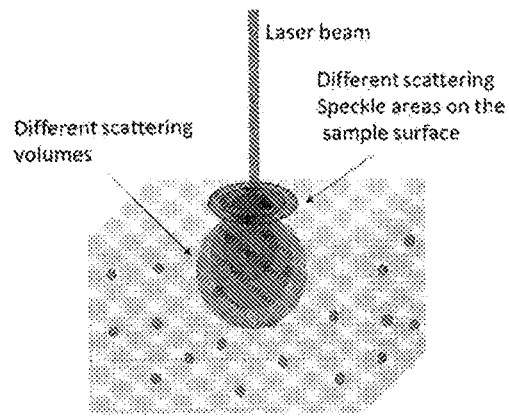

The use of varying aperture unit for enabling depth resolving monitoring of a sample is based on the inventors' understanding that in biological samples, intrinsic particles undergo extensive Brownian excursions and frequently modify the trajectories of photons scattered from inside the sample. Accordingly, light components that penetrate deeper into the sample, generally undergo additional scattering events and accordingly may be emitted from the surface of the sample at axial location further from the poison where the light components impinging on the sample. This is exemplified in FIGS. 9A and 9B. FIG. 9A illustrates a laser light beam impinging at certain location on a sample, and short and long trajectory photons undergoing series of scattering event. The axial location of the photon when it exits the sample and propagated can be represented by random walk statistics, i.e. the distance between the point of exit from the sample and the impinging point changes with number of scattering events (and accordingly depth of penetration) and square root of the number of scattering events. FIG. 9B illustrates the relation between distance from impinging point and depth of penetration of light in the form of scattering volume of light components collected from different scattering areas.

Accordingly, in some examples, the depth resolving module 300, and its aperture unit 310, is configured for selectively controlling spot size of illumination on the inspection region R. Utilizing this configuration, the system may be operated for collecting data about the inspection region using a first (e.g. smaller) spot size, increase the spot size for additional session of data collection (e.g. collection of sufficient frames for determining data about the sample, e.g. about 1-5 seconds and corresponding number of frames) and repeat the collection for a selected number of spot sizes. In this configuration, the collection field of view is preferably smaller than the spot size, and light reflected from the sample may preferably be collected from a point within the illuminated spot. Generally specular reflections may be blocked using one or more polarizers.

Alternatively, the illumination unit 200 may be configured for illuminate a selected spot size on the inspection region, and the aperture unit 310 may be configured for selectively affecting field of view of the collection unit 500. Using this configuration, the system may operate for collecting data about the sample at first (e.g. small) field of view, vary the field of view and collect additional set of image data pieces as required for determining desired data parameters about the sample, and proceed for a selected number of field of view values.

Figure 10:
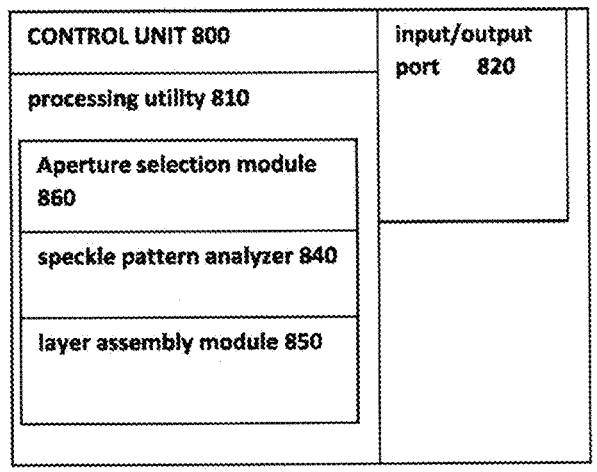
FIG. 10 schematically illustrates a control unit configured for operating with a varying aperture unit according to some embodiments of the invention.

In the above described two configurations, data collected through larger aperture, determining spot size or field of view, is typically indicative of deeper layers of the sample. This is while small aperture data is indicative of shallow layers. Accordingly, the control unit 800 may be operable for collecting sets of image data pieces of different aperture sizes, e.g. for similar stimulation, and determined variation of sample parameters in accordance with depth of penetration of light, by determining variation between the collected sets of image data pieces. FIG. 10 exemplifies the control unit 800 according to these embodiments. As shown, the processing utility 810 may include an aperture selection module, configured for controlling and operating the varying aperture unit 310 of the depth resolving module 300 and vary aperture (illumination spot or collection field of view) between sessions of data collection.

Figure 11A:
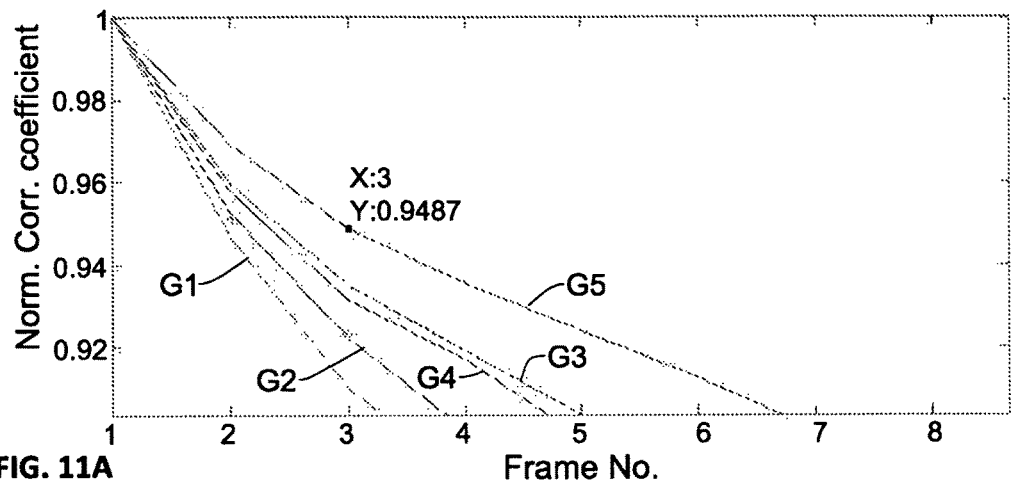
FIGS. 11A and 11B show experimental measurements of speckle patterns correlation for different spot sizes of illumination for low viscosity (FIG. 11A) and high viscosity (FIG. 11B) samples.
Figure 11B:
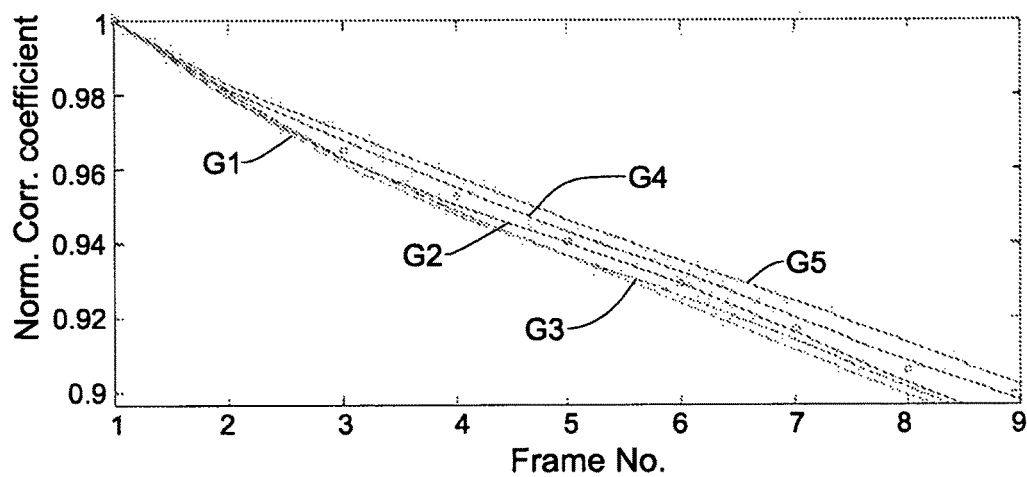

Generally, the speckle-based monitoring techniques utilizes correlation between different speckle patterns. The time dependent speckle fluctuations can be determined by calculating the autocorrelation function g2(t):

$$g_2(t) = \left\{ \frac{\langle I(t_0)I(t_0+t)\rangle}{\sqrt{\langle I(t_0)^2\rangle\langle I(t_0+t)^2\rangle}} \right\} \quad \text{(equation 20)}$$

Where I is the intensity field of each collected speckle pattern, $t_0$ is certain time/frame, and t is a difference between two frames being correlated. The speckle pattern generally decorrelate (reduce in correlation) overtime, where a decorrelation time constant, τ, can be determined by fitting a single exponential function. The present technique utilizes tracking of speckle fluctuations with varying (and slightly reduced) scattered area around the entrance beam by putting controllable aperture controlling spot size or field of view of collection. This results in receiving photons that have pass through different volumes in the sample bulk and accordingly pass through different number of scatters Reference is made to FIGS. 11A and 11B showing calculated correlation functions $g_2(t)$ for speckles collected from different scattered, controlled by iris aperture variation. FIG. 11A shows measurement on low-viscosity sample with iris apertures of 3 mm (G1), 2.5 nn (G2), 2 mm (marked by circles), 1.5 mm (G3), 1 mm (G4) and 0.5 mm (G5), FIG. 11B shows similar measurements for high viscosity sample with similar iris apertures. As can be seen from the figures, the time decay of speckle correlations varies between aperture sizes, where generally for larger aperture sizes, the correlation between speckle patters decay faster. This indicated higher scattering, associated with light penetration to deeper layers of the sample.

Figure 12:
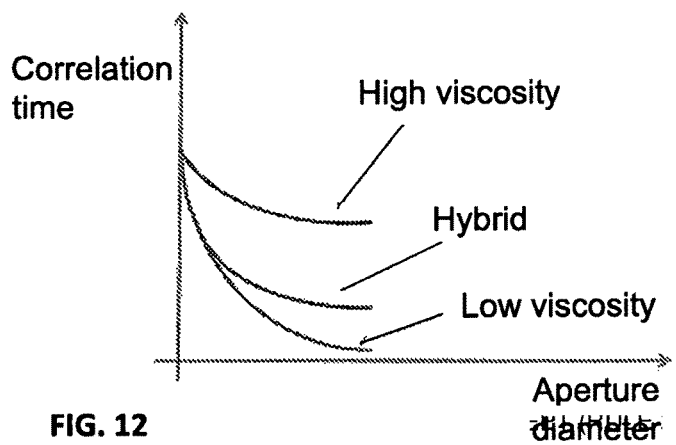
FIG. 12 illustrates general behavior of speckle correlation variation for different illumination apertures for varying viscosity samples.

This technique may be used for characterizing sample including several layers of depth into the sample. Additionally, in some embodiments, this data may be used for characterizing various layers having different viscosity (e.g. layers of lower viscosity under or above layers with higher viscosity) FIG. 12 illustrates different behavior of correlation time in response to variation of aperture size as a result of sample viscosity. This enables determining viscosity data of inner layers of the sample while not being limited to interface layers.

Figure 13:
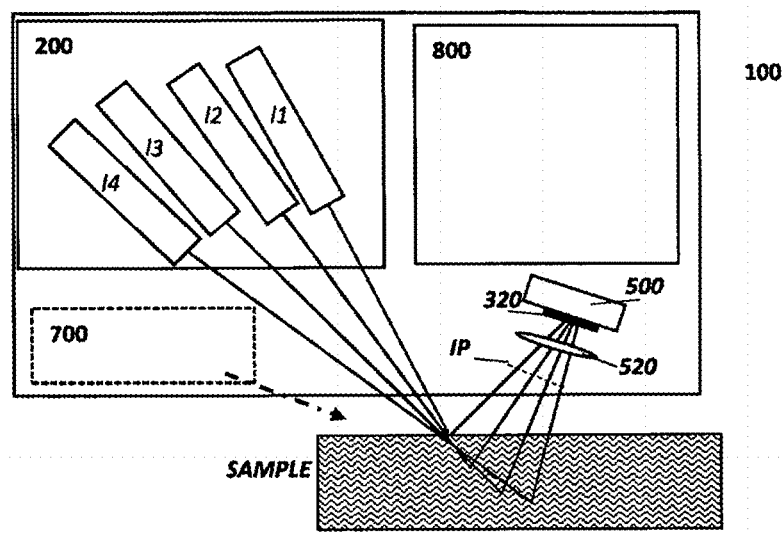
FIG. 13 illustrates monitoring system utilizing angular variation for depth resolving according to some embodiments of the invention.

According to yet additional embodiments of the invention, the present technique enables surface and depth resolved monitoring of sample parameters (e.g. elastographic measurements of a sample) utilizing angular scattering variation effects. Reference is made to FIG. 13 illustrating a system 100 according to some embodiments. The system 100 utilizes an illumination unit 200 including a plurality of light source units I1-I4, configured for providing coherent illumination of a corresponding plurality of different wavelength ranges. The illumination unit 200 is configured for directing light of the plurality of wavelength ranges to impinge on the inspection region with various of angular directions. Accordingly, this technique of the invention utilizes angular scattering from various different layers, or depths, within the sample to collect and determined data indicative of shape variations of a sample as well as sample response to external stimulation, and utilizes different wavelength ranges to enable separation of light components associated with different layer/angular directions.

The system 100 thus includes an illumination unit 200 providing a light source assembly and carrying a plurality (e.g. two, three or more) of light sources, I1-I4 in this example. Each of the light sources is configured to emit coherent illumination with a selected predetermined wavelength range with a corresponding selected angular direction toward the sample. The system further includes a collection unit 500 comprising an optical detector, e.g. pixel array, capable of separating input data based on wavelength in accordance with the plurality of selected wavelength ranges of the light sources (e.g. utilizing a depth resolving module in the form of a polychromatic filter 320 such as Bayer filter), and an optical arrangement 520 configured for collecting light returning from the sample and transmit it to the detector unit. The optical arrangement 520 is configured to provide defocused image of the light returning from the sample, i.e. to generate on the detector surface an image corresponding to an intermediate plane IP between the sample and the optical arrangement.

Figure 14:
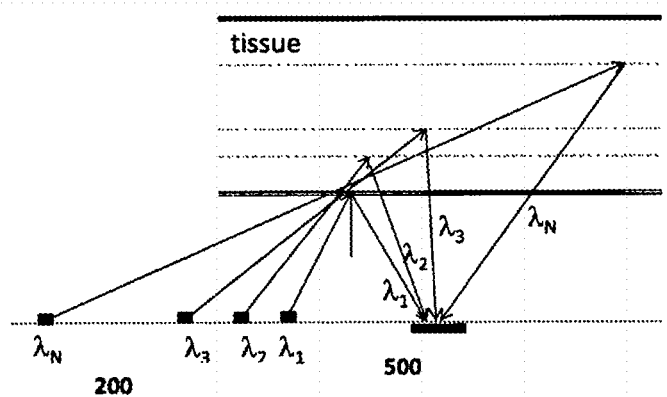
FIG. 14 is an illustration of the wavelength coding used in order to extract depth information.
Figure 15:
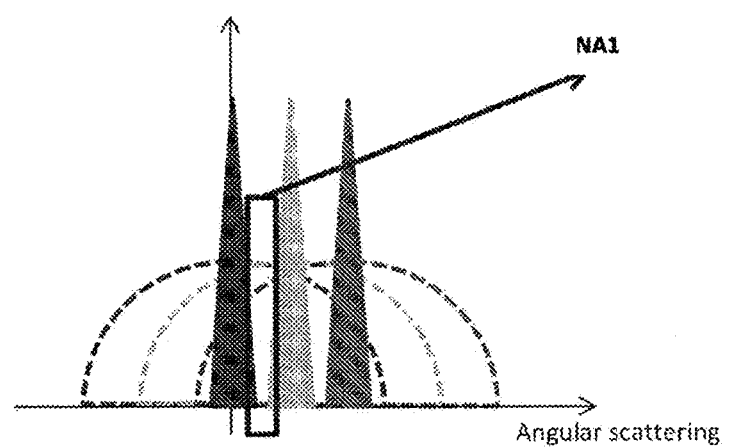
FIG. 15 is an illustration describing variation of angular scattering with respect to depth of penetration.

Generally, the technique exemplified herein with respect to FIGS. 13 to 15 is based on the inventors' understanding that each tissue has a given angular scattering that may vary in accordance with depth. More specifically, at different depth layers of the tissue the angular scattering of light can be defined by an angular range per depth measure S (measured in rad/mm). The technique of the invention, utilizes illumination of a selected location on a tissue with a set of light sources such that each light source has a different wavelength range to allow separation of the returning light. The light sources are typically collimated, or nearly collimated, and are directed at the sample to provide that light scattered from different depths of the sample can be collected by a single optical arrangement having limited NA. The light sources may be arranged with angular separation between the sources, selected such to correspond to maximal angular scattering produced by the maximal depth of the tissue (maximal depth based on desired measurement and/or penetration of the suitable wavelength). In some configurations, the light sources may be configured to be parallel to each other, to thereby enable collection of light scattered from different depths at a common angular range.

Accordingly, the technique also utilizes a light collection unit 500 comprising a sensor array and an optical arrangement 520. The optical arrangement 520 is configured to collect light returning from the inspection region of the sample with relatively low numerical aperture (NA) and direct the collected light onto the sensor array. The optical arrangement is further configured to provide defocused image of the collected light on the sensor array, or more specifically, to image an intermediate plane on the sensor array. This results with an image, on the detector array, being indicative of a secondary speckle pattern generated from the scattered light. As the light source assembly provides coherent illumination in a plurality of wavelength ranges, the collected image data corresponds to a superposition of plurality of speckle patterns respectively.

The detector unit is typically operated to collect a sequence of image data pieces at a selected sampling rate. Each image data piece is transmitted to the control unit 800 and separated to spectral content (wavelengths) with respect to the set of plurality of wavelength ranges of the light sources I1-I4. For each wavelength, the corresponding image data component generally includes data about speckle pattern of light of the corresponding wavelength scattered from certain depth within the sample. The control unit is further configured an operable for processing received data about speckle patterns and determined correlation between different data pieces of speckle patterns to thereby determine parameters of the sample.

The numerical aperture of the optical arrangement 520 is preferably selected to be sufficiently low to provide that for each wavelength range, the range of scattering angles is sufficiently narrow and is thus indicative of certain penetration depth into the sample. The control unit may further comprise a memory utility carrying data indicative of the angular range per depth measure S of the sample (material related data). The control unit may thus utilize this data in the form of a look-up table providing data about depth of scattering source for each collection angle. Or, in the case where the light sources are configured with parallel optical axes, and light is collected with a narrow collection angle, depth of scattering for each wavelength of emitted light. Thus, for each wavelength, the tissue depth from which the collected photons have arrived is determined by:

$$Z_\lambda = \frac{\Delta\theta_\lambda}{S} \qquad \text{(equation 21)}$$

Where $\Delta\theta_\lambda$ is the angular scattering range, which is wavelength ($\lambda$) dependent and determined by NA and alignment of the optical arrangement for collection of light and $Z_\lambda$ is the estimated depth in the tissue from where the scattered photons have arrived (it is also wavelength dependent). Thus, using suitable arrangement of the light sources of the illumination unit 200 and the optical arrangement 520 for collection of light, speckles patterns of different wavelength ranges provide data about sample parameters within different depths of the sample.

Typically, the wavelength ranges used are to be selected within a relatively narrow band, having substantially similar physical and optical properties with respect to the sample material. Moreover, the scattering characteristics (angular range S) may be wavelength dependent, and thus the band of wavelength ranges is preferably selected to provide small and negligible variations in scattering properties. For example, the technique of the invention may provide depth mapping of a few nanometers penetration into the sample, e.g. 50 nm, or more. The depth mapping and depth resolution is typically determined in accordance with penetration range of the wavelength ranges used, number of different wavelength ranges and NA and arrangement of the light source assembly.

As indicated above FIG. 13 illustrating schematically a configuration of a system according to some embodiment of the invention, utilizing angular scattering variation for resolving depth data of a sample. The system 100 includes a light source unit 200 including a plurality of two or more light sources (e.g. in this example four light sources are illustrated I1-I4), each of the light sources is configured to emit coherent illumination with a predetermined wavelength range, different than that of the other light sources. For example, the light sources I1-I4 may be configured to emit light in blue, green, yellow and red colors, thereby enabling separation of input collected light based on wavelength ranges using a suitable color filter (e.g. modified Bayer filter). Accordingly, light returning from the sample is collected by the collection unit 500 including a detector array. The detector array may be associated with suitable wavelength filter 320 (or dispersion grating), associated with the depth resolving module, that enables separation of light components of the different wavelengths. The light collection unit 500 is shown as including an optical imaging arrangement 520 providing imaging of an intermediate plane (defocused with respect to the inspection region).

The optical lens arrangement 520 is configured for collecting data with a predetermined field of view and NA, and generate image data corresponding to an intermediated plane IP onto the detector. This forms image data corresponding to a secondary speckle pattern on the detector array. The system also includes a control/processing unit 800 configured for receiving a sequence of collected image data pieces and for processing of variations in the speckle patterns between the image data pieces.

Accordingly, the detector 500 is configured to transmit data indicative of a plurality of image data pieces, each corresponding with a set of speckle patterns in the selected wavelength ranges. The control unit 800 utilizes color/wavelength variation in the collected data, e.g. by separating each image data piece to wavelength portions and determining correlations between consecutive image data pieces with respect to each wavelength range. Accordingly, the correlation functions determined for each wavelength provide data indicative of a layer of the sample corresponding with angular direction of impinging light of the corresponding wavelength.

In some embodiments and as described above, the system may also include a stimulating unit 700 configured to generate predetermined stimulation onto the sample. The stimulating unit may for example be an ultra sound generator or other acoustic vibration generator or it may apply physical stimulation by contact with the sample. The use of the stimulating unit enable detection of sample response to predetermined stimulation enabling elastographic measurements of the sample.

FIG. 14 illustrates variation in angular scattering direction as a result of different penetration depths. As shown, light of several light sources, having corresponding different wavelength ranges $\lambda_1$ to $\lambda_N$. Different depths of penetrations into the sample return scattered light at different angular distribution. Thus, if the different light sources are aligned such that they all have axis center coincide such that the back scattered light coming from each one of them contribute light to the same detector but light coming from different depths. The light of each light source will return in a predetermined angular distribution to be collected by the optical arrangement from a different depth in the sample. Therefore, each wavelength range can be configured to provide data indicative of a corresponding depth within the sample.

The wavelength/depth separation according to the present invention is further exemplified in FIG. 15 showing spectral analysis with respect to angular scattering from the sample. The spectral analysis of the detector may utilize a dispersion grating (or pixelated filter array) enabling separation between collected light components based on wavelength ranges. Typically, a dispassion grating diverts light components of different wavelength towards different regions of the detector array, while pixelated filter array allows transmission of light of predetermined wavelength range into each of the detector array's pixels. The use of relatively narrow field of view (or numerical aperture) of light collection enables collection of light between peaks of scattering. The collection at NA1 angular region may be sued for distinguishing between light components arriving with different angular direction. This enables detection of light components with plurality of angular distributions corresponding to different depth layers of the sample.

Generally, the technique and system of the present invention as described above may be used to provide depth related analysis of samples and in particular of biological tissues with respect to various mechanical properties, including elastography. The system may be desk mounted and configured to inspect tissues positioned on a sample folding mount, or be configured to be located on or within a probe to enable inspection with cavities of a biological tissue, animal or a human. Thus, the system may be mounted on a probe inserted into a patient's blood stream in the form of a micro-endoscope to enable mapping of internal cavities etc.

Figure 16:
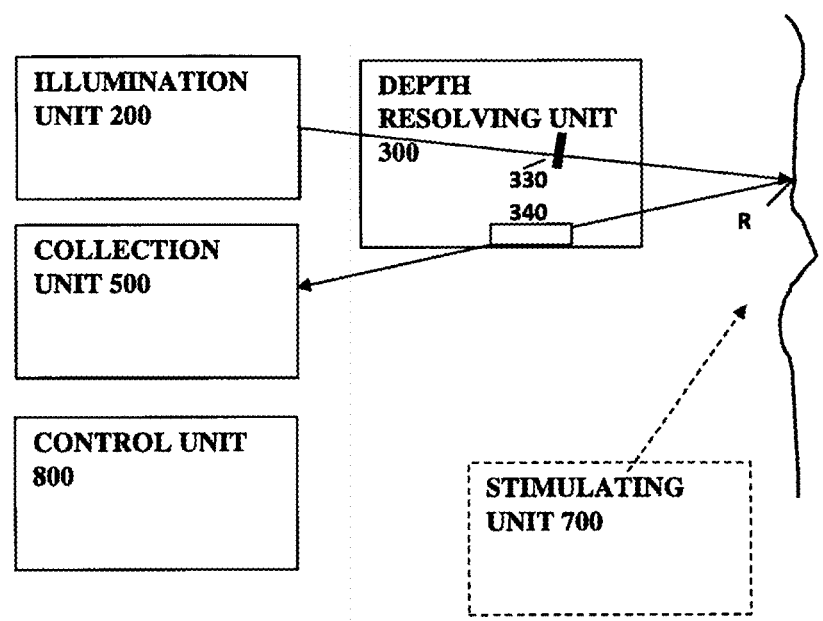
FIG. 16 illustrates a system utilizing degree of polarization data for determining depth data of collected light according to some embodiments of the invention.

In addition to the above described wavelength-depth encoding technique, the technique of the present invention may also utilize polarization-depth encoding. In this configuration, reference is made to FIG. 16 illustrating a system 100 configured for monitoring depth related data of a sample. The system 100 is based on the spackle-based monitoring systems described above, however in this configuration, the depth resolving module 300 includes a polarization measurement unit 340 configured for analyzing degree of polarization (DOP) of collected light. In this connection, the illumination unit 200 may be configured to provide coherent polarize illumination, or utilize a polarizer 330 (which may be associated with the depth resolving module 300). The control unit 800 may be further configured for receiving data about degree of polarization of the collected light from the polarization measurement unit 340 for determining data on penetration depth of the collected light and accordingly on layer to which one or more image data pieces is associated.

Generally, as light scattering causes loss of polarization information, the more the light is scattered i.e. if it is coming from deeper and deeper layers then its degree of polarization is decreased. To this end, the polarization measurement unit 340 is configured for analyzing polarization information of collected light (i.e. include a polarimeter detector) such that the collection unit 500 provides data on light intensity pattern (in the form of speckle pattern) and the depth resolving module 300 provides data on the degree of polarization (DOP), e.g. by analyzing the Stokes parameters. The collected data in the form of sequence of image data pieces and DOP data for each frame is transmitted to the control unit for processing and analyzing. The control unit may determine Stokes parameters of the collected light and accordingly determined a degree of polarization (or degree of polarization loss) for light collected in each frame. The so determined polarization data is used for determining data on depth or layer to which each data piece is associated to thereby construct a depth resolved correlation function and accordingly various parameters of the sample as described above.

The polarization measurement unit 340 may be generally be configured for determining levels of linear polarization along vertical and horizontal axes (and intermediate axes such as 45 and −45 degrees), and clockwise and counter-clockwise circular polarization. The control unit may utilize the data on Stokes parameters for determining DOP of light components as:

$$DOP = \frac{\sqrt{S_1^2 + S_2^2 + S_3^2}}{S_0} = \frac{P_{polarized}}{P_{polarized} + P_{unpolarized}} \quad \text{(equation 22)}$$

where $S_0$, $S_1$, $S_2$, $S_3$ represent the 4 Stokes parameters and $S_0$ is the total power of the inspected light.

It should be noted that the present technique, as described above, with respect to its different embodiments utilizing modulation of reference beam, aperture variation, one or more wavelength of illumination, varying angular distribution of light reflection, and/or measurement of degree of polarization, for determining depth penetration of light components may further include a use of contrast material injected into the sample for enhancing differentiation between layers of the sample. Such contrast material may for example include nanoparticales and/or dye molecule, having varying light reflection and scattering propertied. The contrast material may be inserted/injected into the sample and vary interaction of the sample material with illuminated light impinging thereon in accordance with the concertation of the contrast material. Generally various nanoparticles, die molecules and other contrast materials provide reflection or scattering properties the vary for light of different wavelength or polarization, thereby enhancing variation between light components returning from different layers of the sample.

Generally, the contrast material may be injected locally and allowed to be diffused/distributed into the sample, thereby providing concertation variation between layers. For example smaller nanoparticles typically penetrate deeper into the tissue enabling the use of nanoparticles of different sizes for forming gradient of light reflection/scattering properties. The contrast material may also have time dependent properties expressed via thermal effects (heating with laser) or via acoustic effects (photo acoustic) allowing differentiation of light components that vary in time.

Thus, the core technique of the present invention provides for determining parameters of a sample using interferometric speckle detection while modulating optical path of the reference beam. This provides speckle patterns data indicative of sample parameters corresponding to a plurality of penetration depths of light illuminating the sample. The technique is thereby capable of providing three-dimensional data about the sample and vibrations existing in its different volumetric layers.

The invention claimed is:

1. A system for use in optical measurement of a sample, the system comprising:
   an illumination unit configured for providing coherent illumination of one or more selected wavelength ranges and directing the coherent illumination onto one or more selected inspection regions of the sample,
   a collection unit configured for collecting light returning from the inspection region and generating output data comprising a sequence of image data pieces indicative of secondary speckle patterns formed at an intermediate plane located between the inspection region and the collection unit,
   a depth resolving module comprising an interferometric unit having at least one sample arm and at least one reference arm, the reference arm is configured for receiving a reference illumination beam from the illumination unit, and configured for temporally modulating optical path of said reference arm and combining light propagating in said reference arm with collected light returning from the inspection region, thereby causing the collection unit for collecting image data piece associated with interfering speckle patterns generated by interference between light returning from the sample through a sample arm and a reference beam travelling thorough said reference arm, said coding forms an association between data in the collected secondary speckle patterns and depth layers of the sample at the inspection region; and
   a control unit being connectable to said depth resolving module and configured and operable operating said depth resolving module and for receiving said sequence of image data pieces from the collection unit and processing and analyzing said sequence of image data pieces by determining correlation functions between at least portions of said secondary speckle patterns associated with corresponding depth layers of the sample, and for determining one or more parameter variations along depth of the sample at said one or more inspection region, wherein said control unit comprises a flickering detection module configured and operable for receiving said sequence of image data pieces and identifying at least one portion of image data piece having repetitive flickering and for marking speckle pattern associated with said at least one portion of the frames as relating to depth layer in accordance with frequency of said repetitive flickering, thereby enabling separate processing of speckle pattern portions associated with separate depth layers of the sample.

2. The system of claim 1, further comprising a stimulating unit configured for applying a predetermined stimulation onto the sample to thereby enable detection of sample response to said predetermined stimulation.

3. The system of claim 1, wherein optical path modulation of the reference arm is provided by varying location of a mirror of the reference arm within a predetermined axial range.

4. The system of claim 3, wherein said location of said mirror being moved at constant acceleration along one direction of the axial range and is returned to its original location.

5. The system of claim 1, wherein said optical path of the reference arm being modulated at a selected frequency selected to complete at least one modulation circle within integration time of the collection unit.

6. The system of claim 1, wherein alignment of illumination and collection along the sample arm is configured to provide depth independent interference pattern within one or more speckles.

7. The system of claim 1, wherein said depth resolving module is configured and operable to temporally modulate an optical path of the reference arm, wherein the modulation of the optical path of the reference is selected to provide an orthogonal temporal code, thereby providing orthogonal variation of speckle flickering associated with said orthogonal temporal code for different penetrations depths.

8. A system for use in optical measurement of a sample, the system comprising:
   an illumination unit a plurality of light sources emitting coherent illumination of corresponding plurality of different wavelength ranges and having plurality of optical axes respectively, said illumination unit is configured for providing coherent illumination of said plurality of different wavelength ranges and directing the coherent illumination onto one or more selected inspection regions of the sample;

a collection unit configured for collecting light returning from the inspection region and generating output data comprising a sequence of polychromatic image data pieces corresponding to a secondary speckle patterns of said light returning from the sample collected at a predetermined sampling rate;

a depth resolving module comprising a pre-processing utility and configured an operable to separate data corresponding with speckle patterns of different wavelength ranges from image data pieces of said sequence; and a control unit being connectable to said depth resolving module and configured and operable operating said depth resolving module and for receiving said sequence of image data pieces from the collection unit and processing and analyzing said sequence of image data pieces by determining corresponding correlation functions between at least portions of said secondary speckle patterns of said different wavelength range and or determining one or more parameter variations along depth of the sample at said one or more inspection region.

9. The system of claim 8, wherein said plurality of wavelength ranges having different penetration depths into the sample in accordance with optical parameters of the sample.

10. A system for use in optical measurement of a sample, the system comprising:

an illumination unit configured for providing coherent illumination of one or more selected wavelength ranges and directing the coherent illumination onto one or more selected inspection regions of the sample, a collection unit configured for collecting light returning from the inspection region and generating output data comprising a sequence of image data pieces indicative of secondary speckle patterns formed at an intermediate plane located between the inspection region and the collection unit, a depth resolving module comprising an aperture variation module configured for affecting aperture of at least one of the illumination unit and collection unit, said depth resolving module is configured and operable for affecting aperture of said at least one of the illumination unit and the collection unit thereby forming determining an association between data in the collected secondary speckle patterns and depth layers of the sample at the inspection region; and a control unit being connectable to said depth resolving module and configured and operable to operate said depth resolving module and receive said sequence of image data pieces from the collection unit and processing and analyze said sequence of image data pieces by determining correlation functions between at least portions of said secondary speckle patterns associated with corresponding depth layers of the sample, and to determine one or more parameter variations along depth of the sample at said one or more inspection region.

11. The system of claim 10, wherein said illumination unit is configured for illumination said inspection region forming an illumination spot of a selected dimension, said depth resolving module comprises a varying aperture unit configured for selectively varying field of view of said collection unit.

12. The system of claim 11, wherein said selectively varying field of view being smaller with respect to dimension of said illumination spot.

13. The system of claim 10, wherein said depth resolving module comprises a varying aperture unit configured for selectively varying illumination spot generated by said illumination unit on said inspection region, said collection unit is configured for collecting light returning from said inspection region with a field of view of a selected dimension.

14. The system of claim 13, wherein said field of view is larger with respect to dimension of the illumination spot.

15. The system of claim 1, wherein said illumination unit is configured for providing coherent illumination of predetermined polarization level, said depth resolving module comprises a polarization measurement unit configured and operable for determining data indicative of degree of polarization of collected light; the control unit is further configured and operable for receiving said data indicative of degree of polarization and determine depth level associated to image data piece in accordance with level of loos of polarization of the collected light.

16. The system of claim 15, wherein said polarization measurement unit is configured for providing data indicative of Stokes parameters of collected light.

17. The system of claim 1, wherein said association between data in the collected secondary speckle patterns and depth layers of the sample at the inspection region is enhanced by variation of concertation of one or more selected contrast materials injected into the sample.

* * * * *